United States Patent
Guebitz et al.

(10) Patent No.: US 10,702,607 B2
(45) Date of Patent: Jul. 7, 2020

(54) ABUSE-DETERRENT PHARMACEUTICAL COMPOSITIONS

(71) Applicant: G.L. PHARMA GMBH, Lannach (AT)

(72) Inventors: Georg Guebitz, Hart bei Graz (AT); Katrin Greimel, Vienna (AT); Martin Brandauer, Vienna (AT); Daniela Huber, Hollabrunn (AT); Klaus Bleymaier, Vienna (AT); Wolfgang Kroutil, Graz (AT); Doris Lechner, Graz (AT); Christof Wachter, Lannach (AT); Harald Wagner, Graz (AT); Heimo Winkler, Graz (AT)

(73) Assignee: G.L. PHARMA GMBH, Lannach (AT)

( * ) Notice: Subject to any disclaimer, the term of this patent is extended or adjusted under 35 U.S.C. 154(b) by 0 days.

(21) Appl. No.: 16/079,919

(22) PCT Filed: Feb. 28, 2017

(86) PCT No.: PCT/EP2017/054610
§ 371 (c)(1),
(2) Date: Aug. 24, 2018

(87) PCT Pub. No.: WO2017/148924
PCT Pub. Date: Sep. 8, 2017

(65) Prior Publication Data
US 2019/0060470 A1    Feb. 28, 2019

(30) Foreign Application Priority Data
Feb. 29, 2016    (EP) ................................. 16157803

(51) Int. Cl.
| | |
|---|---|
| *A61K 9/20* | (2006.01) |
| *A61K 31/485* | (2006.01) |
| *A61K 47/42* | (2017.01) |
| *A61K 47/36* | (2006.01) |
| *A61K 9/16* | (2006.01) |
| *A61K 9/14* | (2006.01) |
| *A61K 31/192* | (2006.01) |
| *A61K 31/196* | (2006.01) |
| *A61K 31/167* | (2006.01) |

(52) U.S. Cl.
CPC ............... *A61K 47/42* (2013.01); *A61K 9/14* (2013.01); *A61K 9/16* (2013.01); *A61K 9/20* (2013.01); *A61K 31/167* (2013.01); *A61K 31/192* (2013.01); *A61K 31/196* (2013.01); *A61K 31/485* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 4,299,916 A * | 11/1981 | Litman | G01N 33/52 422/534 |
| 2006/0177380 A1 | 8/2006 | Emigh et al. | |
| 2009/0005565 A1* | 1/2009 | Carroll | C07D 451/06 546/46 |
| 2012/0178773 A1 | 7/2012 | Jenkins et al. | |
| 2013/0195982 A1* | 8/2013 | Pettersson | A61K 9/006 424/490 |

FOREIGN PATENT DOCUMENTS

| | | |
|---|---|---|
| AU | 2012201450 A1 | 4/2012 |
| WO | WO 2006/058249 A2 | 6/2006 |

OTHER PUBLICATIONS

International Search Report dated Apr. 10, 2017 in PCT/EP2017/054610, 3 pages.
Rodriguez-Delgado, M.M., et al., "Laccase-based biosensors for detection of phenolic compounds", Trends in Analytical Chemistry, vol. 74, 2015, pp. 21-45.
Bauer, C.G. et al., "New enzyme sensors for morphine and codeine based on morphine dehydrogenase and laccase", Fresenius J. Anal. Chem., vol. 364, 1999, pp. 179-183.
Sun, W.Q., et al., "Stability of Dry Liposomes in Sugar Glasses", Biophysical Journal, vol. 70, Apr. 1996, 1769-1776.
Riva, S., "Laccases: blue enzymes for green chemistry", Trends in Biotechnology, vol. 24 No. 5, May 2006, pp. 219-226.
Rovve, et al., "Handbook of Pharmaceutical Excipients", 6th Edition, Pharmaceutical Press, 2009, Polymethacrylates, pp. 525-533.
Rowe, et al., "Handbook of Pharmaceutical Excipients", 6th Edition, Pharmaceutical Press, 2009, Ethylcellulose, pp. 262-267.
Schaeffer, T., "Abuse-Deterrent Formulations, an Evolving Technology Against the Abuse and Misuse of Opioid Analgesics", J. Med. Toxicol., 2012, vol. 8, 400-407.
Laemmli, U.K., "Cleavage of Structural Proteins during the Assembly of the Head of Bacteriophage T4", Nature, vol. 227, Aug. 15, 1970, pp. 680-685.
Thomas, K., et al., "A multi-laboratory evaluation of a common in vitro pepsin digestion assay protocol used in assessing the safety of novel proteins", Regulatory Toxicology and Pharmacology, vol. 39, 2004, pp. 87-98.
Chilean Office Action and Search Report dated Jul. 15, 2019, in Patent Application No. 2018-002462, 10 pages (with English Translation of Category of Cited Documents).

* cited by examiner

*Primary Examiner* — Jennifer A Berrios
(74) *Attorney, Agent, or Firm* — Oblon, McClelland, Maier & Neustadt, L.L.P.

(57) ABSTRACT

Disclosed are pharmaceutical compositions comprising oxycodone and an oxycodone-processing enzyme, wherein oxycodone is contained in the pharmaceutical composition in a storage stable, enzyme-reactive state and under conditions wherein no enzymatic activity acts on oxycodone.

12 Claims, 10 Drawing Sheets

ABUSE-DETERRENT PHARMACEUTICAL COMPOSITIONS

The present application relates to abuse-deterrent pharmaceutical compositions comprising oxycodone.

Prescription opioid products are an important component of modern pain management. However, abuse and misuse of these products have created a serious and growing public health problem. One potentially important step towards the goal of creating safer opioid analgesics has been the development of opioids that are formulated to deter abuse. The development of these products is considered e.g. by the US FDA as a high public health priority (see "Abuse-Deterrent Opioids—Evaluation and Labeling"; Guidance for Industry FDA April 2015, FDA; "FDA Guidance").

Because opioid products are often manipulated for purposes of abuse by different routes of administration or to defeat extended-release (ER) properties, most abuse-deterrent technologies developed to date are intended to make manipulation more difficult or to make abuse of the manipulated product less attractive or less rewarding. It should be noted that these technologies have not yet proven successful at deterring the most common form of abuse—swallowing a number of intact capsules or tablets to achieve a feeling of euphoria. Moreover, the fact that a product has abuse-deterrent properties does not mean that there is no risk of abuse. It means, rather, that the risk of abuse is lower than it would be without such properties. Because opioid products must in the end be able to deliver the opioid to the patient, there may always be some abuse of these products.

In the FDA Guidance, abuse-deterrent properties are defined as those properties shown to meaningfully deter abuse, even if they do not fully prevent abuse. The term abuse is defined as the intentional, non-therapeutic use of a drug product or substance, even once, to achieve a desirable psychological or physiological effect. Abuse is not the same as misuse, which refers to the intentional therapeutic use of a drug product in an inappropriate way and specifically excludes the definition of abuse. The FDA Guidance uses the term "abuse-deterrent" rather than "tamper-resistant" because the latter term refers to, or is used in connection with, packaging requirements applicable to certain classes of drugs, devices, and cosmetics.

The science of abuse deterrence is relatively new, and both the formulation technologies and the analytical, clinical, and statistical methods for evaluating those technologies are rapidly evolving. The FDA Guidance identifies seven categories of abuse-deterrent formulations:

1. Physical/chemical barriers—Physical barriers can prevent chewing, crushing, cutting, grating, or grinding of the dosage form. Chemical barriers, such as gelling agents, can resist extraction of the opioid using common solvents like water, simulated biological media, alcohol, or other organic solvents. Physical and chemical barriers can limit drug release following mechanical manipulation, or change the physical form of a drug, rendering it less amenable to abuse.

2. Agonist/antagonist combinations—An opioid antagonist can be added to interfere with, reduce, or defeat the euphoria associated with abuse. The antagonist can be sequestered and released only upon manipulation of the product. For example, a drug product can be formulated such that the substance that acts as an antagonist is not clinically active when the product is swallowed (i.e. administered in the intended way and intact), but becomes active if the product is crushed and injected or snorted.

3. Aversion—Substances can be added to the product to produce an unpleasant effect if the dosage form is manipulated or is used at a higher dosage than directed. For example, the formulation can include a substance irritating to the nasal mucosa if ground and snorted.

4. Delivery System (including use of depot injectable formulations and implants)—Certain drug release designs or the method of drug delivery can offer resistance to abuse. For example, sustained-release depot injectable formulation or a subcutaneous implant may be difficult to manipulate.

5. New molecular entities and prodrugs—The properties of a new molecular entity (NME) or prodrug could include the need for enzymatic activation, different receptor binding profiles, slower penetration into the central nervous system, or other novel effects. Prodrugs with abuse-deterrent properties could provide a chemical barrier to the in vitro conversion to the parent opioid, which may deter the abuse of the parent opioid. New molecular entities and prodrugs are subject to evaluation of abuse potential for purposes of the Controlled Substances Act (CSA).

6. Combination—Two or more of the above methods could be combined to deter abuse.

7. Novel approaches—This category encompasses novel approaches or technologies that are not captured in the previous categories.

Although there are already a number of proposals available based on the categories 1 to 5, above, there is still an unmet need to provide efficient combinations of these methods and approaches and, especially, to provide novel approaches.

The article of Rodriguez-Delgado et al. (Trends Anal. Chem. 74 (2015): p. 21-45) discloses laccase-based biosensors for the detection of phenolic compounds in food industry and for environmental and medical applications, i.a. a Clark oxygen electrode with immobilized laccase (Bauer et al., Fresenius J. Anal. Chem. 364 (1999); 179-183).

WO 98/18909 A1 discloses a transgenic organism transformed with an enzyme that is capable of transferring reducing equivalents between pyridine nucleotide cofactors.

EP 0 032 286 A2, U.S. Pat. Nos. 3,852,157 A and 4,391,904 A disclose methods for analysis for a member of an immunological pair using a test surface, i.a. a morphine: horseradish peroxidase conjugate and a carboxymethyl-morphine:glyoxate reductase, to detect antibodies in a sample.

WO 2012/122422 A2 and US 2011/262359 A1 disclose active agent prodrugs with heterocyclic linkers which may be cleaved enzymatically by a gastrointestinal enzyme once the prodrug has entered the gastrointestinal tract after oral ingestion. For providing the drug from the prodrug, the action of the enzyme is needed to cleave the prodrug to controllably release the drug. The provision of such prodrugs is also used to deter abuse of the actual drug.

US 2014/330021 A1 discloses aryl carboxylic acids chemically conjugated to hydromorphone as a strategy to deter abuse.

US 2005/176644 A1 and US 2012/178773 A1 disclose oxycodone derivates with a chemical moiety coupled to oxycodone to deter abuse or to substantially decrease the pharmacological activity of oxycodone.

AU 2012/201 450 A1 and WO 2006/058249 A2 refer to abuse deterrent oral dosage formulations comprising a gel forming polymer, a nasal mucosal irritating surfactant and a flushing agent together with the drug with abuse potential.

All these documents relate to common and known strategies to deter abuse of these drugs with abuse potential, such as oxycodone.

The prior art on unrelated fields discloses various compositions wherein enzymes are combined with agents or compositions for various uses:

WO 00/27204 A1 relates to an antimicrobial composition comprising an oxidoreductase and an enhancing agent of the N-hydroxyanilide-type. The compositions according to WO 00/27204 A1 are intended as detergent or cleaning compositions but also for the use as disinfectants or for the preservation of paints, food, beverages, etc.

WO 01/98518 A2 relates to methods for transforming biologically active ingredients, such as antibiotics, by laccases and manganese peroxidase enzymes. According to WO 01/98518 A2, known active ingredients should be transformed by laccases/manganese peroxidases to introduce additional functional groups to arrive at new active substances with modified properties (e.g. to overcome resistances against certain antibiotics).

EP 0 919 628 A1 discloses a method for "macromolecularizing" phenolic compounds or aromatic amine compounds by the action of enzymes with a polyphenol oxidizing activity such as laccase. EP 919 628 A1 therefore also discloses an enzymatic method to transform certain substances, including antimicrobial agents or viral infection inhibitors, to substances with higher molecular weight which may then be used as thickeners, stabilizers but also antimicrobial agents or viral infection inhibitors. It is also suggested to treat waste water for eliminating the phenolic compounds or aromatic amine compounds by macromolecularization. EP 0 919 628 A1 suggest laccase, catechol oxidase, polyphenol oxidase, ascorbic acid oxidase or bilirubin oxidase as enzymes which can be (industrially) used for the method disclosed.

WO 97/41215 A1 relates to industrial enzymes technology and the problem concerning storage/delivery of such enzymes. These enzymes are either delivered in dry form (where dust formation is reported to be a disadvantage) or liquid formulations (which have two disadvantages: that enzymes are not storage stable and present in their active state i.e. reacting with a substrate). In preventing this premature action with a substrate, WO 97/41215 A1 suggests to provide the enzyme and the substrate in a substantially water free liquid composition which would react in aqueous conditions but not react in the water free liquid composition.

DE 10 2006 048 833 A1 discloses a pharmaceutical preparation for the treatment of osteoporosis which comprises, in addition to collagen and a calcium-containing substance (as main active substance), a crosslinking agent which comprises crosslinking agents (for example polyhydroxyaromatics) and a catalyst of the crosslinking reaction (for example, an enzyme such as laccase) which is capable of crosslinking the crosslinking agents. The aim of DE 10 2006 048 833 A1 is to establish a three-dimensional matrix for bone support ("liquid bone").

WO 97/27841 A1 relates to stabilized enzyme formulations which can be stored and easily made available by means of a two-component dispensing system ("dispenser"). This document therefore relates generally to the provision of enzymes such as (for example) oxidoreductases or proteases, for example in cleaning fluids, shampoos or vitamin preparations.

WO 2005/063037 relates to chewing gums which may contain enzymes. The enzymes are incorporated into the chewing gum due to their catalyzing effect on degradation. Virtually all possible enzymes are listed in this document without annotation ("pairing") with other substances. The chewing gum of WO 2005/063037 may further contain a pharmaceutically, cosmetically or biologically active substance, selected from a huge list of substances without any correlation to the enzyme.

Also WO 2007/143989 A1 is drawn to a chewing gum which comprises a biodegradable polymer and (i.a.) an enzyme which is comprised in the chewing gum as a hydrophobic enzyme formulation. Again, the enzyme is provided for degrading the (biodegradable polymer in the) chewing gum. Provision of the enzyme in a hydrophobic enzyme formulation is therefore made for preventing a premature degradation.

WO 2012/003367 A2 relates to a drug delivery method, wherein a nonwoven web with a plurality of filaments contains an active agent wherein the release of the active agent from the filament may be triggered by an enzyme. This nonwoven filament is not suitable for oral ingestion.

WO 00/02464 A1 refers to a process for the treatment of tobacco, by using a phenoloxidizing enzyme in order to oxidize phenolic compounds in tobacco.

Oxycodone ((5R,9R,13S,14S)-4,5α-epoxy-14-hydroxy-3-methoxy-17-methylmorphinan-6-one) is a semisynthetic opioid synthesized from thebaine, an opioid alkaloid found in the Persian poppy and one of the many opioid alkaloids found in the opium poppy. It is used to relieve moderate to severe pain. Oxycodone acts on the central nervous system (CNS) to relieve pain. It belongs to the group of medicines called narcotic analgesics (pain medicines). Oxycodone is marketed i.a. under the trade names Roxicodone®, OxyContin®, Oxecta®, OxyIR®, Endone®, Oxynorm®, and OxyNEO®.

Oxycodone is one of the most used narcotic analgesics with over 100 tons manufactured per year. Usually, the US accounts for most of its world-wide consumption (more than 80%).

Similar to other opioid analgesics, oxycodone has a high risk of abuse, because it tends to induce feelings of euphoria, relaxation and reduced anxiety. It is therefore not surprising that oxycodone is the most commonly abused pharmaceutical drug in the United States. It is estimated that oxycodone is used by at least 11 million people in the US at least once in a "non-medical way". About 100.000 patients per year are admitted to US hospitals due to misuse of this drug; about 10.000 deaths a year are caused by its abuse in the US. Accordingly, oxycodone is one of the major targets for the FDA Guidance mentioned above. For the time being, abuse-preventive measures have been included in the following oxycodone products: The short-acting oxycodone preparation of Pfizer (marketed as OXECTA®) contains inactive ingredients, referred to as tamper-resistant AVERSION® Technology, making crushing, chewing, snorting, or injecting the opioid impractical because of a change in its chemical properties (FDA approval for relabelling the reformulated version as abuse-resistant was granted in June 2011). In the long-acting oxycodone line of Purdue Pharma, the composition was reformulated (marketed as OxyContin® CR) by using the "INTAC® polymer" to make the pills extremely difficult to crush or dissolve in water to reduce OxyContin® abuse (FDA approval for relabelling the reformulated version as abuse-resistant was granted in April 2013).

It is therefore the object of the present invention to provide a new approach and technology for abuse-deterrent oxycodone formulations.

Therefore, the present invention provides a pharmaceutical composition comprising oxycodone and an oxycodone-processing enzyme, wherein oxycodone is contained in the pharmaceutical composition in a storage stable, enzyme-reactive state and under conditions wherein no enzymatic activity acts on oxycodone.

As summarised above, oxycodone (IUPAC name: (5R,9R,13S,14S)-4,5α-epoxy-14-hydroxy-3-methoxy-17-methylmorphinan-6-one) is a well-known drug which is also available in salt form, preferably as hydrochloride, bitartrate, tartrate, camphorsulphonate, phenylpriopionate, sulphate, phosphate, pectinate, methyiodide, hydroiodide and terephthalate. "Oxycodone" according to the present invention includes therefore all pharmaceutically marketed forms thereof, especially also all pharmaceutically acceptable salt forms. The present invention also relates to prodrug forms of oxycodone as e.g. disclosed in EP 2 663 187 A.

The present invention provides a new category of abuse-deterrent strategy (a "novel approach") which offers a practical toolbox for virtually all pharmaceutical compositions where a risk for abuse is present or has to be assumed. Such a principle has not yet been proposed or suggested in the prior art. Accordingly, no prior art composition (e.g. those referred to above) has proposed or suggested a composition comprising oxycodone and an oxycodone-processing enzyme, wherein oxycodone is contained in the pharmaceutical composition in a storage stable, enzyme-reactive state and under conditions wherein no enzymatic activity acts on oxycodone.

The abuse-deterrent principle is—for each and every drug—the same: the drug with the abuse risk is combined together with one or more enzymes (optionally also with necessary cofactors/cosubstrates/mediators) in the pharmaceutical preparation in a storage stable (usually dry) state wherein the enzyme is activatable (i.e. providing the enzyme in an enzyme-reactive state); but wherein the enzyme in the pharmaceutical preparation is contained under conditions not allowing enzymatic activity act on drug. Accordingly, there may be e.g. a spatial or reactional separation in the pharmaceutical composition. This principle is therefore also specifically suited for oxycodone.

If the drug is administered as intended—e.g. by ingestion of a tablet—the enzyme is inactivated (in case of orally administered compositions preferably by the acidic environment in the stomach and/or proteolytically active enzymes present in the GI-tract). If the drug is abused by trying to extract the active substance (oxycodone) from such pharmaceutical compositions, the enzyme becomes active and acts on the drug (oxycodone) so as to process the drug into another compound which is either completely unusable anymore or has—at least—a lower abuse potential and therefore lowers the motivation for abuse (i.e. making the pharmaceutical composition according to the present invention abuse-deterrent).

The present invention therefore provides the combination of oxycodone and an oxycodone-processing enzyme which is activated once the composition according to the present invention is treated by abusive measures which aim at extracting oxycodone from the present pharmaceutical composition. Whereas the compositions according to the present invention are usually destined for oral administration, extraction of oxycodone in an abusive manner is usually performed with the aim of providing (intravenously) injectable compositions. Oxycodone-processing enzymes are known in principle; virtually all enzymes which process oxycodone with or without additional cofactors/cosubstrates/mediators are suitable in the composition according to the present invention, if they can be appropriately manufactured and can be provided in the composition with an activity (upon dissolving in aqueous solvents) that is able to process oxycodone in an appropriate manner. Enzymes are known to catalyse more than 5,000 biochemical reaction types. Enzymes according to the present invention may require additional components so that they can act on oxycodone according to the present invention. For example, the enzymes according to the present invention may need cofactors, cosubstrates and/or mediators. A mediator is usually a substance that transfers electrons but acts as catalyst (or in a similar manner as a catalyst). A cosubstrate participates (stoichiometrically) in the reaction (with oxycodone). Cofactors are "helper molecules" that assist the enzyme in the process of reacting in the biochemical transformation with oxycodone. Accordingly, the present invention applies reactions where an enzyme catalyses oxidation or reduction of mediator compound which oxidizes or reduces oxycodone; where an enzyme catalyses binding of co-substrates to oxycodone; as well as where a second enzyme (or further enzymes) catalyses the transformation of activated oxycodone.

Preferred oxycodone-processing enzymes are those that are specific for the various functional groups of oxycodone, i.e. the methoxy-group at C3, the epoxy-group between C4 and C5, the oxo-Group at C6, and the methyl group at the N-atom at position 17. These preferred enzymes therefore include oxidoreductases (especially monooxygenases), transferases (such as acetylases, sulfotransferases and glucuronosyltransferases), and hydrolases, especially epoxide hydrolases. Preferred enzymes are therefore enzymes that catalyse O-demethylation, N-demethylation, keto-reduction, N-oxidation, rearrangement of the ketone to an ester (Baeyer-Villiger reaction; the ketone is transformed by a monooxygenase to an ester (e.g. also a cyclic ketone to a lactone)), epoxy-hydroxylation of oxycodone or addition of molecules (such as glucuronidation, sulfation and acetylation) to oxycodone. O-demethylation primarily results in a transformation of the methoxy-group into a hydroxy-group, which may then further react by addition of further molecules (including di- or polymerization) or further oxidation. Further reaction may also be catalysed by a second enzyme. N-demethylation primarily results in a secondary amine group, which may then further react by addition of further molecules (including di- or polymerization) or further oxidation. Again, further reaction may also be catalysed by a second enzyme. Keto-reduction results in a transformation of the keto-group into a hydroxy-group, which may then further react by addition of further molecules (including di- or polymerization) or further oxidation. Again, further reaction may also be catalysed by a second enzyme. N-oxidation leads to an N-oxide compound, which may either directly lead to an inactivation of oxycodone or then further react by addition of further molecules (including di- or polymerization). Epoxy-hydroxylation results in dihydrodiols (often: trans-dihydrodiols), which may then further react by addition of further molecules (including di- or polymerization) or further oxidation. Addition of molecules (such as sulfation, glucuronidation and acetylation, but also including di- or polymerization) leads to products that are often insoluble or are deprived of their abusive potential due to accelerated excretion potential). In these reaction synthetic substrates (e.g. in glucoronidation) may be added to enhance inactivation of oxycodone.

With such enzymes oxycodone is processed to an inactive form or—at least—to agents which are less active than oxycodone and therefore are less attractive for those who intend to abuse the pharmaceutical oxycodone compositions.

Examples of known oxycodone-processing enzymes are NAD(P)(H)-dependent oxidoreductases, such as the oxycodone reducing enzymes from the aldo-keto reductase (AKR) superfamily, especially AKR1C1 (20 alpha-hydroxysteroid dehydrogenase (EC 1.1.1.149)), AKR1C2 and AKR1C4. A specifically preferred oxycodone processing enzyme is 3-alpha-hydroxysteroid 3-dehydrogenase (EC 1.1.1.213). The NAD(P)(H)-dependent oxidoreductases transform oxycodone in the presence of NAD(P)H into its reduced degradation product. Another preferred group of oxycodone-processing enzymes are the keto-steroid reductases, such as the 3-, 6- and 17-ketosteroid reductases.

According to a preferred embodiment, the oxycodone-processing enzyme is a monooxygenase. Monooxygenases have the ability to insert one oxygen atom into various organic substrates. Molecular oxygen needs to be activated in order to carry out this type of reaction and to do so, electrons are transferred from (in)organic cofactors to the molecular oxygen. A wide range of oxidative reactions are catalysed by monooxygenases like hydroxylations from aliphatic and aromatic compounds, epoxidations from alkenes, Baeyer-Villiger oxidations, sulfoxidations, amine oxidations, selenide oxidations, halogenations, phosphite ester oxidations and organoboron oxidations.

Monooxygenases are divided into the following families: Cytochrome P450 monooxygenases or heme-dependent monooxygenases (EC 1.14.13, EC 1.14.14, EC 1.14.15) is the best known and largest family of monooxygenases and mainly present in eukaryotic (mammals, plants, fungi) as well as bacterial genomes and are able to hydroxylate non-activated carbon atoms. Non-heme iron-dependent monooxygenases (EC 1.14.16) catalyse hydroxylation and epoxidation reactions and utilize two iron atoms as cofactor. Enzymes that belong to this family include alkene monooxygenases, phenol hydroxylases, membrane-bound alkane hydroxylases as well as aromatic monooxygenases. Copper-dependent monooxygenases (EC 1.14.17 and EC 1.14.18) represent a rather small family of enzymes, requiring copper ions for hydroxylation of the substrates. Flavin-dependent monooxygenases (EC 1.13.12 and EC 1.14.13) are mostly found in prokaryotic genomes and are known to catalyse epoxidations, Baeyer-Villiger oxidations and halogenations. Additionally, several new types of monooxygenases were discovered that catalyse hydroxylations without being cofactor-dependent (Cofactor-independent monooxygenases) but accept only a restricted range of substrates. On the other hand the uncoupling reaction can be reversed; this mechanism is present in the catalytic cycle of some monooxygenases to use hydrogen peroxide to yield the oxidative enzyme intermediate. A more universal and well established approach involves regeneration of NAD(P)H. Both chemical and enzyme based regeneration is currently used. Chemical regeneration may use a rhodium-complex catalyst together with formate as substrate which is oxidized to carbon dioxide. Thereby, electrons are transferred NAD(P)$^+$ reducing the coenzyme. Likewise, enzymatic regeneration of NAD(P)H is well established and is based on a large variety of NAD(P)$^+$-dependent dehydrogenases like formate dehydrogenase or glucose-6-phosphate dehydrogenase.

According to a further preferred embodiment, the oxycodone-processing enzyme is a peroxidase or peroxygenase (EC 1.11.1 and 1.11.2). Fungal unspecific peroxygenases (EC 1.11.2.1) are able to oxyfunctionalise various compounds by transferring peroxide-borne oxygen to diverse substrates. The catalyzed reactions are similar to those that are catalyzed by cytochrome P450 monooxygenases and include hydroxylations of aliphatic compounds, epoxidations of linear, branched and cyclic alkenes, dealkylations, oxidations of aromatic and heterocyclic compounds as well as oxidations of organic hetero atoms and inorganic halides.

Phenolic products are a product of aromatic peroxygenations and these phenols can subsequently be subjects of coupling and polymerization reactions via their corresponding phenoxyl radicals due to the peroxidative activity of the enzymes. These enzymes are mostly found in Basidiomycota and Ascomycota (e.g. *Agrocybe aegerita, Coprinellus radians, Marasmius rotula*) but also Mucoromycotina, Chytridiomycota, Glomeromycota as well as Oomycota whereas no indication was found that they are present in plants, animals or prokaryotes. The needed hydrogen peroxide can be produced in situ by a variety of oxidases like glucose oxidase (EC 1.1.3.4), cellobiose dehydrogenase (EC 1.1.99.18) or lactate oxidase(EC 1.1.3.2), enzymes that produce $H_2O_2$ upon oxidizing substrates like glucose, oligossacharides, polysaccharides, lactate and others many of which are present in formulations.

Specifically preferred further enzymes that are used as oxycodone-processing enzymes according to the present invention include the following ones:

O-demethylation (C3): Cytochrome P450 (EC 1.14; +heme+an H-donor, such as NAD(P)H, especially CYP2C subfamily; CYP2D6; unspecific monooxygenase (EC 1.14.14.1; +NAD(P)H), Codeine 3-O-demethylase (CODM; EC 1.14.11.32; +2-oxogutarate (+$O_2$)); thebaine 6-O-demethylase (T6ODM; EC 1.14.11.31; +2-oxoglutarate (+$O_2$)); Peroxidases and peroxygenases (EC 1.11.1 and EC 1.11.2; +$H_2O_2$), especially horseradish peroxidase (HRP, EC 1.11.1.7; +$H_2O_2$) and fungal unspecific peroxygenases (EC 1.11.2.1).

Preferably, O-demethylation is combined with further processing steps, because it is possible that oxymorphone, alpha- and beta-oxymorphol or other oxymorphone-like products can result in such O-demethylation of oxycodone. Since oxymorphone could have similar abuse-potential as oxycodone, a further step (i.e. processing by a further, oxymorphone-processing enzyme) may be provided, such as a glucuronidation step.

N-demethylation (N17): CYP1-3 (all: EC 1.14.14.1; +heme+H-donor, such as NAD(P)H, FAD, FMN, ferredoxin, etc.), preferably CYP3A, CYP1A, CYP2B, CYP2C and CYP2D, especially CYP3A4, CYP3A5, CYP3A7, CYP1A2, CYP2B6, CYP2C9, CYP2C19, and CYP2D6, especially CYP3A4 and CYP3A5. Peroxidases (EC 1.11.1 and EC 1.11.2; +$H_2O_2$), horseradish peroxidase (HRP, EC 1.11.1.7; +$H_2O_2$). N-demethylation may lead to products such as noroxycodone, noroxymorphone, alpha- and beta-noroxycodol, or similar products with no or low abusive potential (although having a certain (but very low) opioid agonist activity, but far less than oxycodone (also due to their poor uptake into the brain)).

Keto-reduction (C6): carbonyl reductase (NADPH) (EC 1.1.1.184; +NAD(P)H), such as dihydromorphinone ketone reductase (DMKR; types I to V) and dihydrocodeinone ketone reductase (DCKR, types I and II); additionally dehydrogenases such as morphine 6-dehydrogenase (EC 1.1.1.218; +NAD(P)H). Keto-reduction may lead to products, such as alpha- and beta-oxycodol, or nor-6-oxycodol, which have no (or only a weak) abusive potential.

N-oxidation (N): Flavin-containing monooxygenase (EC 1.14.13.8; +NAD(P), FAD).

Epoxy-hydroxylation: microsomal epoxide hydrolase (EC 3.3.2.9), epoxide hydratase (EC 3.3.2.3 and 4.2.1.63), soluble epoxide hydrolase (EC 3.3.2.10).

Glucuronidation: UDP-glucuronosyltransferase (EC 2.4.1.17; +UDP-glucuronate), especially UGT1 and UGT2 enzymes, such as UGT1.1, UGT2B7, bilirubin-glucuronoside glucuronosyltransferase (EC 2.4.1.95; +UDP-glucuronate). In all cases synthetic functionalised co-substrates may be used e.g. instead of UDP-glucuronate to better promote inactivation of oxycodone may be added.

Acetylation: ac(et)yltransferase (EC 2.3) and CoA-transferase (E.C. 2.8.3), especially N-acetyltransferase (NAT, EC 2.3.1; usually +acetyl-Coenzyme A (ac-CoA)) and O-acetyl-transferase (OAT; EC 2.3.1; usually +ac-CoA).

Sulfation: sulfotransferases (EC 2.8.2), especially the human SULT transferases.

Preferably, oxymorphone is subjected to phenol-oxidation at C3 by laccases (EC 1.10.3.2) and related enzymes: e.g. catecholoxidases (EC 1.10.3.1), monophenol monooxygenases (EC 1.14.18.1), ascorbate oxidases (EC 1.10.3.3), peroxidases e.g. horseradish peroxidase (EC 1.11.1.7); N-dealkylation by mixed function oxidase Cyt.P450 (CYP3A4; CYP2C8), monooxygenases (EC 1.14), peroxidases e.g. horseradish peroxidase (EC 1.11.1.7); keto-reduction/OH oxidation by 3alpha-hydroxysteroid 3-dehydrogenase (EC 1.1.1.213), NADPH dehydrogenase (OYE); N-oxidation at N17 by peroxidases/peroxygenases (EC 1.11), FAD-monooxygenase (EC 1.14.13.8); epoxy-hydration at C4/5 by epoxide hydrolase (EC 3.3.2.9); by other oxygenase activity with an additional introduction of oxygen by phenol hydroxylation by phenol 2-monooxygenase (EC 1.14.13.7); addition of molecules at C3 by glucuronosyl transferases, N-acetyltransferases, sulfotransferases; aldol condensation (dimerization) by aldolases (EC 4.1.2).

Specifically preferred pharmaceutical compositions according to the present invention therefore comprise oxycodone, with an enzyme as described above (as oxycodone-processing enzyme).

A further option to select suitable oxycodone-processing enzymes is to select enzymes disclosed to be effective and specific for a given reaction type (e.g. O-demethylation, N-demethylation, keto-reduction, epoxy-hydoxylation, N-oxidation, or addition of molecules (such as glucuronidation and acetylation)) from enzyme databases, such as the BRENDA (BRaunschweig ENzyme DAtabase) enzyme portal (http://www.brenda-enzymes.org). BRENDA is the main information system of functional biochemical and molecular enzyme data and provides access to seven interconnected databases.

BRENDA contains 2.7 million manually annotated data on enzyme occurrence, function, kinetics and molecular properties. Each entry is connected to a reference and the source organism. Enzyme ligands are stored with their structures and can be accessed via their names, synonyms or via a structure search.

FRENDA (Full Reference ENzyme DAta) and AMENDA (Automatic Mining of ENzyme DAta) are based on text mining methods and represent a complete survey of PubMed abstracts with information on enzymes in different organisms, tissues or organelles. The supplemental database DRENDA provides more than 910 000 new EC number-disease relations in more than 510 000 references from automatic search and a classification of enzyme-disease-related information. KENDA (Kinetic ENzyme DAta), a new amendment extracts and displays kinetic values from PubMed abstracts.

The integration of the EnzymeDetector offers an automatic comparison, evaluation and prediction of enzyme function annotations for prokaryotic genomes. The biochemical reaction database BKM-react contains non-redundant enzyme-catalysed and spontaneous reactions and was developed to facilitate and accelerate the construction of biochemical models.

The oxycodone-processing enzymes often require co-factors, such as H and/or electron donors and acceptors, such as NAD(P)H, FMN, FAD, ferredoxin, 2-oxoglutarate, hemes (CYP superfamily); or donors for the groups to be added to oxycodone (acetyl (such as ac-CoA), glucoronate (such as UDP-glucuronate), etc.). These co-factors are also provided in the composition according to the present invention, unless such factors are, in any way, already present in a potentially abusive situation (e.g. if the composition is dissolved in an aqueous solution, $O_2$ which is required for some of the oxidation reactions disclosed above, or $H_2O$ needed for epoxy-hydroxylation will be available under such abusive conditions; sometimes even the ions needed, provided they are contained in the extraction solvent). In the present specification, co-factors needed for the specific enzymatic reaction with oxycodone (and provided in the present composition, e.g. as prosthetic groups directly connected to the enzyme) are sometimes explicitly mentioned; however, the person skilled in the art is well aware of the co-factors necessary and the conditions suitable for obtaining a composition according to the present invention, wherein enzyme activity is usually optimised to abusive circumstances, e.g. when the composition is dissolved in water or an aqueous buffer.

In some embodiments, it can be preferred to provide a combination of enzymes (and their respective co-factors) in the preparation according to the present invention. For example, it can be preferred to add further processing enzymes, such as UDP-glucuronosyltransferase and/or acetyltransferases to further process the oxycodone-products that emerge from O-demethylation, N-demethylation, keto-reduction, epoxy-hydroxylation or N-oxidation, e.g. by providing a glucuronidated/acetylated derivate at the newly created hydroxyl-group. Such combinations may also be applied if the result of the oxycodone-processing itself represents a potential aim of abuse (as e.g. for oxymorphone).

If the oxycodone-processing enzyme is a membrane-dependent enzyme, the enzyme may be provided in liposomal form, preferably in the form of dry liposomes (in such cases, auxiliary substances, such as sucrose or trehalose may be preferably added; see e.g. Sun et al., Biophys. J 70 (1996): 1769-1776).

According to a specific embodiment, the pharmaceutical composition according to the present invention comprises a further enzyme, preferably a further oxycodone-processing enzyme or an enzyme further processing the processed oxycodone forms, especially laccase (EC 1.10.3.2).

A specific embodiment of the present invention therefore additionally provides a laccase in the present composition. Laccase can dimerise or polymerise (or initiate or otherwise aid polymerisation of) the oxycodone-processed molecules. Although laccase itself is not directly an oxycodone-processing enzyme (because it does not process oxycodone itself), laccase can be used with oxycodone-processing enzymes disclosed above to further enhance the abuse-deterrent character of the present compositions. Laccase can also be used with electron mediators to directly oxidize oxycodone or with cosubstrates with certain functionalities (phenolic, aromatic amines, double bonds) to form oligomers or polymers preventing abuse. Laccases are also suitable to create hydrogels, specifically when employed with hydrogel-forming components, such as chitosan and/or catechol or carboxymethylchitosan and/or vanillin. Laccases (EC 1.10.3.2; CAS registry number 80498-15-3) are frequently described and analysed copper-containing oxidase enzymes that are found in many plants, fungi, and microorganisms (Riva, Trends in Biotechnology 24 (2006), 219-226). Laccases act on phenols and similar molecules, performing one-electron oxidations. According to the BRENDA database, the systematic name of laccase is benzenediol:oxygen oxidoreductase. Laccases are defined as a group of multi-copper proteins of low specificity acting on both o- and p-quinols, and often acting also on aminophenols and phenylenediamine. The semiquinone may react further either enzymatically or non-enzymatically.

Additionally, some non-laccase substrates can be oxidized by using mediators for the reaction. When these well-established laccase mediators are oxidized by laccase they generate strong oxidizing reactive species (radicals, radical quinones and quinones) which can further react with non-laccase substrates. If the laccase oxidized mediator is reduced back to its original compound, it is again re-oxidized by laccase to generate reactive species which can again oxidize another molecule. Such laccase mediators are able to oxidize molecules which cannot be oxidized directly by laccase. There are many types of mediators used in laccase formulations including aromatic centered mediators (ArOH; e.g. ferulic acid, syringaldehyde) and nitrogen centered mediators (RNOH; e.g. violuric acid, 1-hydroxybenzotriazole.

Suitable mediators are widely available in the present field. For example, mediators capable of enhancing the activity of oxidoreductases, especially of phenol-oxidizing enzymes, such as laccase, are disclosed in WO 95/01426 A1, WO 96/10079 A1 or WO 2012/085016 A1.

Another strategy involves the use of co-substrates together with laccase. Co-substrates are added to the reaction and they are oxidized by the laccase subsequently reacting and forming covalent bonds with non-laccase substrates resulting in oligomers or polymers. Generally many laccase substrates can act as cosubstrates to bind to non-laccases substrates such as phenolics (catechol), aromatic amines, alkenes, etc.

Laccases play a role in the formation of lignin by promoting the oxidative coupling of monolignols, a family of naturally occurring phenols. Laccases can be polymeric, and the enzymatically active form can be a dimer or trimer. Other laccases, such as the ones produced by the fungus *Pleurotus ostreatus*, play a role in the degradation of lignin, and can therefore be included in the broad category of lignin-modifying enzymes. Because laccase belongs to the oxidase enzyme family it requires oxygen as a second substrate for the enzymatic action. Spectrophotometry can be used to detect laccases, using the substrates ABTS (2,2'-azino-bis-(3-ethylbenzthiazoline-6-sulfonic acid), syringaldazine, 2,6-dimethoxyphenol, and dimethyl-p-phenylenediamine. Activity can also be monitored with an oxygen sensor, as the oxidation of the substrate is paired with the reduction of oxygen to water.

The present invention provides the combination of oxycodone with oxycodone-processing enzymes as a novel approach for abuse-deterrent pharmaceutical drug formulations. The new strategy on which the present invention is based is the use of an oxycodone-processing enzyme (or an enzyme system) to convert oxycodone into a non-active form (e.g. into a precipitated or inactivated or less-active product) making it non-useable (e.g. by transforming it into an inactive (or at least: less active) form or by making it impossible to inject the drug with a syringe). On the other hand, if oxycodone is administered as foreseen (e.g. orally), proteases from the body (or the total environment of the stomach and the small intestine) deactivate the oxycodone-processing enzyme and oxycodone can unfold its effect without being inactivated by the accompanying enzyme. For an improved protease-degradability, the oxycodone-processing enzymes may be modified by the introduction of (additional) protease cleavage sites so as to increase the degradation rate of these enzymes after exposure to such proteases.

A prerequisite of the abuse-deterrent strategy according to the present invention is that during storage and before use the composition according to the present invention containing a combination of oxycodone and the oxycodone-processing enzyme is kept in an environment wherein the oxycodone-processing enzyme does not (yet) react with oxycodone. This can e.g. be safeguarded by keeping (storing) both components under conditions where the oxycodone-processing enzyme is inactive or by spatial separation of the two components. For example, if the composition is kept in a dry form, the oxycodone-processing enzyme cannot react with oxycodone because such reaction requires aqueous conditions. As soon as a dry composition according to the present invention is dissolved in water (e.g. in order to extract the opioid drug for abuse), the oxycodone-processing enzyme can react with oxycodone and enzymatically transforms oxycodone into a molecule that is not (ab-)usable anymore because of its degradation or because it is polymerised. Another example for preventing the oxycodone-processing enzyme to react on oxycodone is to spatially separate the oxycodone-processing enzyme from oxycodone so that—again—only after contact of the composition with water or a comparable solvent, the oxycodone-processing enzyme can react on oxycodone. Such spatial separation can e.g. be established by providing the oxycodone-processing enzyme and oxycodone in different compartments of the pharmaceutical formulation, by providing specific coatings, by separate granulation, etc.

On the other hand, the oxycodone-processing enzyme in the compositions according to the present invention must be reactive, e.g. once exposed to aqueous environment or to other situations which are not in line with the administration routes or administration activities intended (i.e. if an abuse is likely), it has to react with the accompanied oxycodone to prevent or at least deter abuse of this drug.

The present pharmaceutical composition can be formulated according to the intended (non-abuse-deterrent) administration route, if necessary, adapted to the present invention (e.g. when the oxycodone-processing enzyme and oxycodone are spatially separated). Preferably, the pharmaceutical composition according to the present invention is provided as a dose unit. It is therefore preferred to provide the present composition as a tablet, e.g. a mini-tablet (i.e. small tablets with a diameter of 3 mm or below), a coat-core tablet (coated tablet), a bi-layer tablet, a multi-layer tablet, an effrerescent tablet, a soluble tablet, a dispersible tablet, a capsule, a pellet, a MUPS (multiple unit pellet system), a granulate, a powder, especially coated, sugar-coated and/or functionally coated (e.g. enteric coated) forms thereof. Enteric coatings are specifically advantageous for the prevention of premature inactivation of the oxycodone-processing enzyme, i.e. before the physiologic proteases act on the oxycodone-processing enzyme. An enteric coating is generally defined as a polymer barrier applied on oral medication for protecting drugs from the acidity of the stomach. Enteric coatings are therefore usually stable at the highly acidic pH found in the stomach, but break down rapidly at a less acidic (relatively more basic; pH 7-9) pH in the intestine (i.e. after leaving the stomach). Typical substances/materials used for such enteric coatings are shellac, cellulose acetate phthalate (CAP), polyvinyl acetate phthalate (PVAP), hydroxypropylmethylcellulose phthalate, and methacrylic acid ester copolymers, or zein, for example, as well as hydrophobic or hydrophilic polymers and mixtures of such substances, if appropriate. Hydrophobic polymeric coatings include acrylic polymer, acrylic copolymer, methacrylic polymer or methacrylic copolymer, including Eudragit® L100, Eudragit® L100-55, Eudragit® L 30D-55, Eudragit® 5100, Eudragit® 4135F, Eudragit® RS, acrylic acid and methacrylic acid copolymers, methyl methacrylate, methyl methacrylate copolymers, ethoxyethyl methacrylates, cyanoethyl methacrylate, aminoalkyl methacrylate copolymer, polyacrylic acid, polymethacrylic acid, methacrylic acid alkylamine copolymer, polymethyl methacrylate, polymethacrylic acid anhydride, polymethacrylate, polyacrylamide, polymethacrylic acid anhydride and glycidyl methacrylate copolymers, an alkylcellulose such as ethylcellulose, methylcellulose, carboxymethyl cellulose, hydroxyalkylcellulose, hydroxypropyl methylcelluloses such as hydroxypropyl methylcellulose phthalate, and hydroxypropyl methylcellulose acetate succinate, cellulose acetate butyrate, cellulose acetate phthalate, and cellulose acetate trimaleate, polyvinyl acetate phthalate, polyester, waxes, shellac, zein, or the like. The coating can also include hydrophilic materials such as a pharmaceutically-acceptable, water-soluble polymer such as polyethylene oxide (PEO), ethylene oxide-propylene oxide co-polymers, polyethylene-polypropylene glycol (e.g. poloxamer), carbomer, polycarbophil, chitosan, polyvinyl pyrrolidone (PVP), polyvinyl alcohol (PVA), hydroxyalkyl celluloses such as hydroxypropyl cellulose (HPC), hydroxyethyl cellulose, hydroxymethyl cellulose and hydroxypropyl methylcellulose, carboxymethyl cellulose, sodium carboxymethyl cellulose, methylcellulose, hydroxyethyl methylcellulose, polyacrylates such as carbomer, polyacrylamides, polymethacrylamides, polyphosphazines, polyoxazolidines, polyhydroxyalkylcarboxylic acids, alginic acid and its derivatives such as carrageenate alginates, ammonium alginate and sodium alginate, starch and starch derivatives, polysaccharides, carboxypolymethylene, polyethylene glycol, gelatin or the like.

Preferred enteric coating materials are methyl acrylate-methacrylic acid copolymers, cellulose acetate succinate, hydroxy propyl methyl cellulose phthalate, hydroxy propyl methyl cellulose acetate succinate, polyvinyl acetate phthalate (PVAP), methyl methacrylate-methacrylic acid copolymers, shellac, cellulose acetate trimellitate, sodium alginate and zein.

A further embodiment of the pharmaceutical composition according to the present invention is a coated composition wherein the coat comprises the oxycodone-processing enzyme. The oxycodone-processing enzyme acts on oxycodone when the coated composition is dissolved in aqueous liquids (for extracting the drugs (opioids)), whereas the oxycodone-processing enzyme is immediately destroyed or inactivated after ingestion (according to the prescribed (oral) administration route) in the stomach or in the intestine.

Since the pharmaceutical preparations according to the present invention are supposed to be administered to human patients in need of the drugs contained therein, the preparations are manufactured and finished as pharmaceutical preparations according to GMP, preferably according to the standards provided by the European Pharmacopoeia. This implies that the pharmaceutical preparations according to the present invention are marketed in properly sterile, clean and appropriately wrapped form as required by the regulatory authorities for marketed drug products, especially as required by the EMA for oxycodone.

A specifically preferred embodiment is a composition wherein the oxycodone-processing enzyme is coated so as to keep the oxycodone-processing enzyme inactive on oxycodone as long as the planned administration route is followed, i.e. which keeps the activity of the oxycodone-processing enzyme from oxycodone while being coated, e.g. until excretion of the (still coated) oxycodone-processing enzyme by the patient, whereas abuse activity destroys the coat so that the oxycodone-processing enzyme immediately acts on oxycodone. For example, the oxycodone-processing enzyme may be coated by one or more of the aforementioned substances/materials used for enteric coatings, e.g. Eudragit® L 30D-55 or Kollicoat® MAE 30D. Specifically preferred examples of such film-coatings or sequestering materials are Eudragit® RS (30D), Eudragit® NE 30 D; ethylcellulose, polymethacrylates (all disclosed in Rowe et al. (Eds.) "Handbook of Pharmaceutical Excipients" $6^{th}$ Ed. (2009), Pharmaceutical Press, pages 262ff., 525 ff.); or the substances used in other opioid compositions for coating opioid antagonists (see e.g. EP 2 034 975 B1, U.S. Pat. No. 8,465,774 B2, and WO 2004/026283 A1), except, of course and self-understanding, substances that have a degradation risk by oxycodone-processing enzyme activity (e.g. because they contain a group that is converted by the oxycodone-processing enzyme provided in the composition according to the present invention).

The pharmaceutical composition preferably contains oxycodone in the amount foreseen in the non-abuse-deterrent original composition. Accordingly, oxycodone is preferably contained in an amount of 0.1 to 5 000 mg (i.e. 0.1 mg to 5 g), preferably 0.5 to 1 000 mg, especially 1 to 500 mg, per dosage unit. Currently marketed pharmaceutical oxycodone preparations contain 2.5, 5, 7.5, 10, 15, 20, 30, 40, 80, 120 or 160 mg, usually as oxycodone hydrochloride. Preferred amounts of oxycodone in such single dosage units may therefore be provided from 0.5 to 500 mg, especially from 1 to 200 mg. Depending on the formulation and the expected activity of the oxycodone-processing enzyme during normal administration, also an increase of the amount of oxycodone may be provided (compared to the non-abuse-deterrent original composition, i.e. to the pharmaceutical formulation of oxycodone without the abuse-deterrent features) e.g. to compensate possible loss of drug activity (if such minor loss of activity is likely or cannot be completely excluded).

The amount of the oxycodone-processing enzyme in the present pharmaceutical composition can be adjusted mainly based on the amount of oxycodone and the formulation details. Illustrative examples to determine the activity of preferred oxycodone-processing enzymes are listed in the example section.

More specifically, the amount of the oxycodone-processing enzyme in the present pharmaceutical composition can be adjusted mainly based on the amount of oxycodone, the reactivity of the enzyme and the formulation details. For example, the oxycodone-processing enzyme may be added in the composition according to the present invention in an amount of 0.1 to 10 000 units (i.e. 0.1 u to 10 ku).

The pharmaceutical compositions according to the present invention are dry compositions, usually with a moisture content (well) below 10%, preferably with a moisture content below 5%, especially below 2%.

The moisture content is preferably determined by accepted methods in the present filed, e.g. by the European Pharmacopoeia. A specifically preferred method for determination of moisture is the Karl Fischer titration method (European Pharmacopeia 8.5 (2015), 2.5.12: semi-determination of water), wherein the water of crystallisation content is included again.

Although the present invention provides a completely new strategy for abuse-deterrent drugs, the present novel approach is also combinable with other abuse-deterrent strategies, e.g. the ones that have been identified in the FDA Guidance 2015 or in Schaeffer, J. Med. Toxicol. 8 (2012), 400-407. Accordingly, the pharmaceutical composition according to the present invention preferably comprises a further abuse-deterrent feature, for example a feature selected from the group consisting of: a physical or chemical barrier, especially increased tablet hardness, a (oxycodone-processing enzyme-insensitive) drug antagonist, an aversion component, an abuse-deterrent delivery system and a prodrug. Provision of a physical barrier, especially increased tablet hardness, or an aversion component, especially a gelling agent and/or a non-gelling viscosity-increasing agent (e.g. λ-carrageenan) or, e.g. an emetic or a nasal irritant, is specifically preferred. For example, the present composition can be provided as a formulation with a resistance of more than 400 N, especially more than 500 N, as prescribed in the European Pharmacopeia (Ph.Eur.[8] (2014) 2.9.8). Further examples for abuse-deterrent features combinable with the present invention are the provision of discrete mechanically reinforcing particles (WO 2012/061779 A1), of materials that are both hydrophilic and hydrophobic (WO 2012/112952 A 1), of an acid soluble ingredient (a cationic polymer) with a buffering ingredient (U.S. Pat. No. 9,101,636 B2), of a monolithic solidified oral dosage form prepared by a thermal process (US 2008/0075771 A1), of an emetic or a nasal irritant (US 2008/075771 A1), of an extruded formulation (US 2015/0057304 A1) or of amorphous or polymeric organic acid salts of the opioid (US 2015/016835 A1), etc.

According to a preferred embodiment the pharmaceutical composition comprises a matrix containing 1 to 80 wt. % of one or more hydrophobic or hydrophilic polymers, preferably a matrix comprising agar, alamic acid, alginic acid, carmellose, carboxymethylcellulose sodium, carbomer (such as Carbopol® carrageenan, chitosan, especially carboxymethylchitosan, catechol, copovidone, dextrin, gelatin, hydroxyethyl cellulose, hydroxypropyl cellulose, hydroxypropyl methylcellulose, methacrylic acid copolymer, methylcellulose derivatives, microcrystalline cellulose, polyacrylic acid, polyalkylene oxide, especially polyethylene glycol, polyvinyl alcohol, polyvinyl acetate, povidone, propylene glycol alginate, a polyvinylcaprolactam-polyvinyl acetate-polyethylene glycol graft co-polymer, pullulan, silicon dioxide, sodium alginate, starch, vinylpyrrolidone-vinyl acetate copolymers; or of non-polymer matrix formers like microcrystalline wax, fatty alcohols and fatty acids like stearyl alcohol, cetyl stearyl alcohol, stearic acid, palmitic acid or salts and mixtures thereof, mono-, di- and triglycerides of saturated fatty acids with a chain length between 16 and 22 carbon atoms and a mixture of such mono- di- and triglycerides, respectively.

According to a preferred embodiment of the present invention, the pharmaceutical composition comprises a hydrogel-forming component and/or suitable crosslinkers which allows the generation of insoluble crosslinked hydrogels of the drug once the oxycodone-processing enzyme is activated by abusive steps (optionally a laccase as disclosed above may also contribute to such crosslinking). Preferred hydrogel-forming components are chitosan and carboxymethylchitosan; preferred crosslinkers are phenolic crosslinkers, especially catechol and vanillin. Preferred examples of such hydrogel/crosslinker compositions are compositions comprising chitosan and catechol or compositions comprising carboxymethylchitosan and vanillin.

The pharmaceutical composition according to the present invention is preferably a storage stable composition, preferably by comprising less than 5%, especially less than 1%, oxycodone-processing enzyme-processed oxycodone degradation products after 6 month storage at 25° C. under dry conditions.

In general, the oxycodone-processing enzymes should be acid-labile so that their activity in the present composition is immediately inactivated as soon as the oxycodone-processing enzyme is in contact with the stomach fluid and/or the intestine environment of the patient to whom the composition is administered.

The present pharmaceutical composition can be provided as a modified release composition, especially a prolonged release composition. The term "modified form" is meant to include accelerated release, controlled release, and sustained release forms. Certain release forms can be characterized by their dissolution profile. "Dissolution profile", means a plot of amount of active ingredient released as a function of time (Ph.Eur.[8] (2014) 2.9.3). The dissolution profile can be measured utilizing the Drug Release Test <724>, which incorporates standard test USP 26 (Test <711>) of the US Pharmacopeia. A profile is characterized by the test conditions selected. Thus, the dissolution profile can be generated at a preselected apparatus, shaft speed, temperature, volume, and pH of the dissolution media. A first dissolution profile can be measured at a pH level approximating that of the stomach. A second dissolution profile can be measured at a pH level approximating that of one point in the intestine or several pH levels approximating multiple points in the intestine. A highly acidic pH may simulate the stomach and a less acidic to basic pH can simulate the intestine. By the term "highly acidic pH" it is meant a pH of about 1 to about 4. By the term "less acidic to basic pH" is meant a pH of greater than about 4 to about 7.5, preferably about 6 to about 7.5. A pH of about 1.2 can be used to simulate the pH of the stomach. A pH of about 6.0 to about 7.5, preferably about 7.5 can be used to simulate the pH of the intestine.

In contrast to modified release, "immediate release" is the conventional or non-modified release form in which greater than or equal to about 50% or more preferably about 75% of a drug according to the present invention is released e.g. within two hours of administration, preferably within one hour of administration, especially within 30 min of administration. By "controlled release" a dosage form is meant in which the drug release is controlled or modified over a period of time. Controlled can mean, for example, accelerated, sustained, delayed or pulsed release at a particular time. Alternatively, controlled can mean that the drug release is extended for longer than it would be in an immediate release dosage for, i.e., at least over several hours.

"Delayed release" indicates that there is a time-delay before significant plasma levels of the drug are achieved. A delayed release formulation according to the present invention avoids an initial burst of the drug, or can be formulated so that drug release in the stomach is avoided. A "pulsed release" formulation can contain a combination of immediate release, sustained release, and/or delayed release formulations in the same dosage form. A "semi-delayed release" formulation is a "pulsed released formulation in which a moderate dosage is provided immediately after administration and a larger dosage some hours after administration.

The terms "sustained release" or "extended release" are meant to include the release of the drug at such a rate that blood (e.g., plasma) levels are maintained within a therapeutic range but below toxic levels for at least about 8 hours, preferably at least about 12 hours, especially at least 24 hours (specifically preferred for 1 per day dosage regimen) after administration at steady-state. The term "steady-state" means that a plasma level for a given drug has been achieved and which is maintained with subsequent doses of the drug at a level which is at or above the minimum effective therapeutic level and is below the minimum toxic or overdose plasma level for a given drug. Most of the polymeric matrices and non-polymer matrix formers mentioned above have the capacity to deliver prolonged or sustained release capacity for a given drug in the formulation according to the present invention.

According to a preferred embodiment, the pharmaceutical composition according to the present invention comprises oxycodone alone (as the only effective ingredient) or in combination with other pharmaceutically active ingredients, preferably in combination with a non-opioid analgesic, especially with ibuprofen, diclofenac, naproxen, paracetamol and acetyl-salicylic acid.

In a preferred embodiment, the enzyme in the pharmaceutical composition essentially does not act on the drug (or any other constituents of the pharmaceutical composition) in vivo when the composition is administered in the intended way and intact (i.e. swallowed intact).

Preferably, the enzyme in the pharmaceutical composition according to the present invention is present in the composition in an essentially non-releasable form when the composition is administered in the intended way and intact (i.e. swallowed intact).

According to a preferred embodiment of the present invention the enzyme in the present pharmaceutical composition is deactivated in vivo.

According to a further aspect, the present invention also relates to a method for manufacturing a pharmaceutical composition according to the present invention comprising the steps of mixing oxycodone or a pharmaceutically acceptable salt, hydrate, solvate, ester or prodrug thereof with the oxycodone-processing enzyme and finishing the mixture to a pharmaceutical composition. Alternatively, the method for manufacturing the pharmaceutical composition according to the present invention comprises the steps of providing oxycodone or a pharmaceutically acceptable salt, hydrate, solvate, ester or prodrug thereof and the oxycodone-processing enzyme in separated form and finishing the separated components to a pharmaceutical composition.

According to another aspect, the present invention provides a composition comprising oxycodone and a hydrogel-forming component and/or a crosslinker. The hydrogel-forming component and/or the crosslinker allow the generation of insoluble crosslinked molecules, especially as hydrogel, of the drug once the pharmaceutical composition is mixed with an aqueous mixture in the process of abusive steps. Preferred hydrogel-forming components are chitosan and carboxymethylchitosan; preferred crosslinkers are phenolic crosslinkers, especially catechol and vanillin. Preferred examples of such hydrogel/crosslinker compositions are composition comprising chitosan and catechol or compositions comprising carboxymethylchitosan and vanillin.

Preferably, the compositions according to the present inventions are provided as hydrogels. This involves the inclusion of another abuse deterrent approach, namely to create a system which changes the rheological properties of the reaction solution, i.e. the formation of a hydrogel. Hydrogels are very viscous and as a consequence, the drawing up with a needle is not possible.

The present invention also relates—by its nature—to a method of administration the (abuse-deterrent) pharmaceutical composition according to the present invention (i.e. comprising oxycodone or a pharmaceutically acceptable salt thereof and an oxycodone-processing enzyme, wherein oxycodone is contained in the pharmaceutical composition in a storage stable, enzyme-reactive state and under conditions wherein no enzymatic activity acts on oxycodone) to a patient in need thereof, wherein the pharmaceutical composition according to the present invention is orally administered to this patient in an effective amount and wherein the oxycodone-processing enzyme is automatically deactivated in the course of this oral administration (by the components present in the patient's gastro-intestinal tract (mouth, esophagus, stomach, and (small) intestine(s))), e.g. by the patient's saliva, gastric juice and intestinal fluids and the patient's enzymes contained therein) so that the oxycodone-processing enzyme does not act on oxycodone and oxycodone can therefore exhibit its destined effect in the patient).

The present invention is further illustrated by the following examples and the figures, yet without being restricted thereto.

FIG. 1 shows the strategy of the present invention. The abuse deterrent oxycodone/oxycodone-processing enzyme system according to the present invention either converts oxycodone into a processed oxycodone derivative with no or low abusive potential or creates in combination with additives a hydrogel with which it is not possible anymore to inject the drug with a syringe. If oxycodone is administered as foreseen, proteases from the body (and the conditions in the stomach and in the small intestine) deactivate the oxycodone-processing enzyme and oxycodone unfolds its effect.

EXAMPLES

Figure 1:
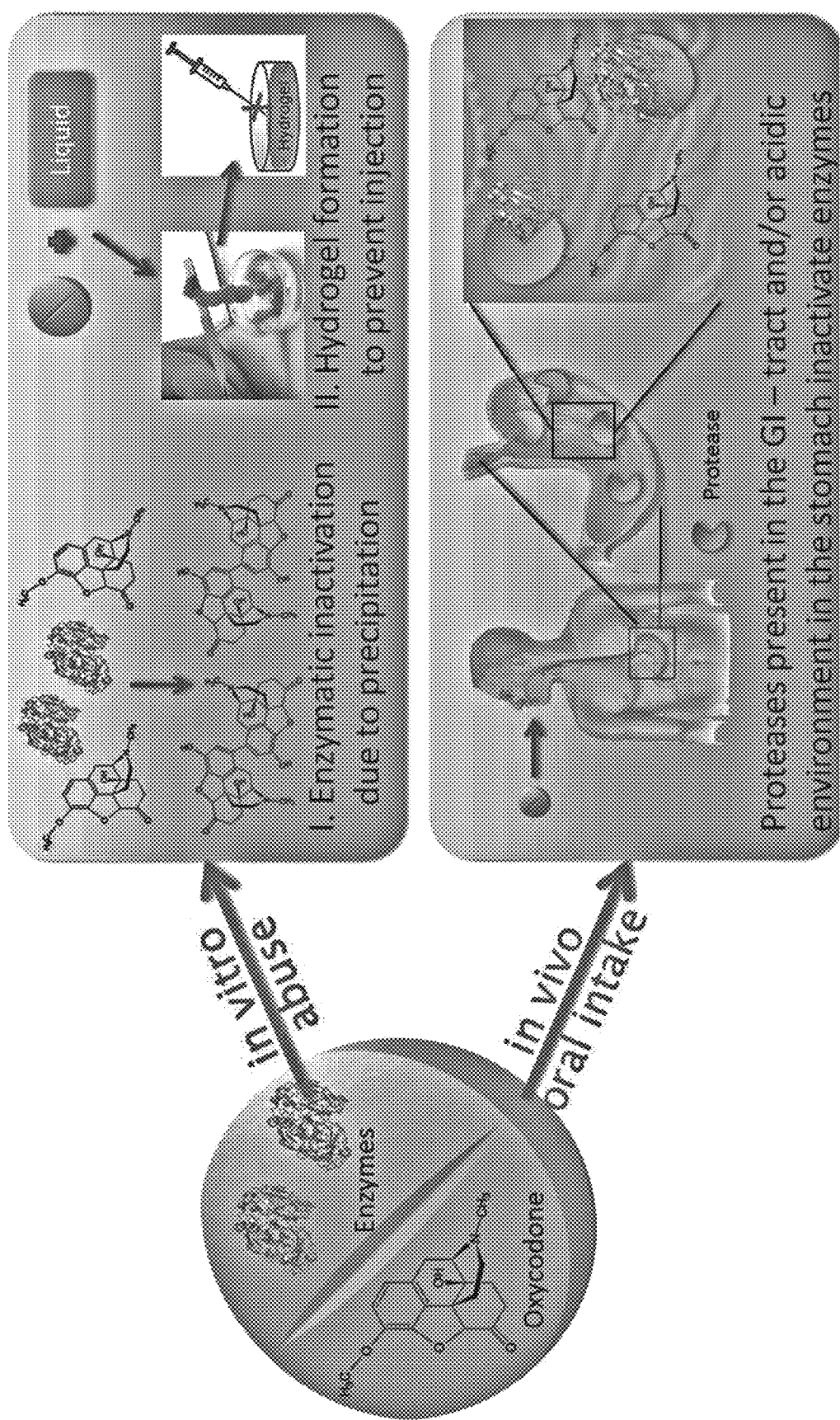
Figure 2:
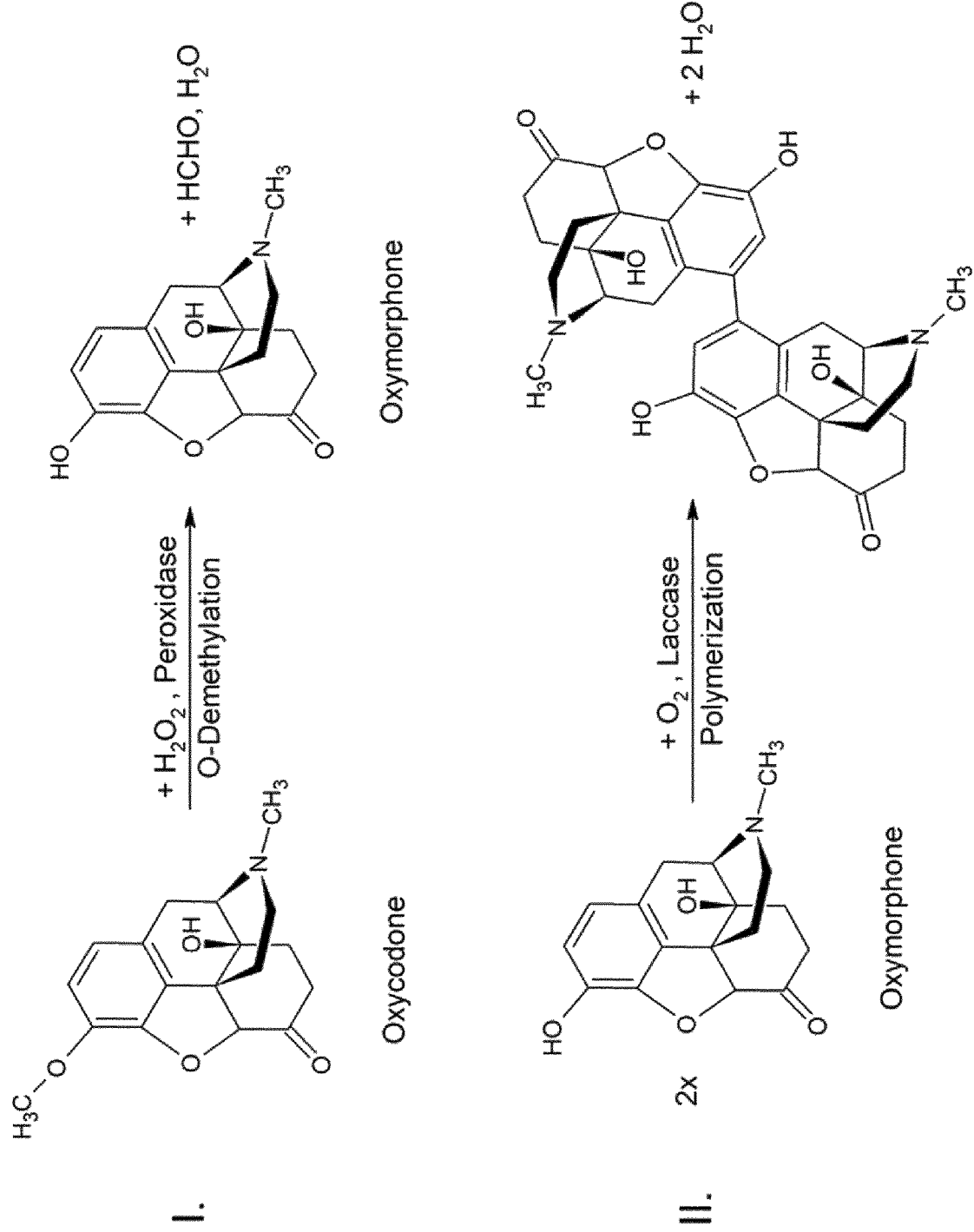
FIG. 2 shows the enzymatic conversion of oxycodone to a partly precipitated product.

1. Inactivation of Oxycodone with an Enzyme System Consisting of Peroxidase/Laccase Opioids are an important component of modern pain management, though the abuse and/or misuse of those drugs have created a growing public health problem. To counteract this problem, there is a strong demand for new technologies for preventing the abuse of opioids. This project therefore tries to approach this problem with a very unique way based on using enzymes.

The potential of enzymes to polymerize opioids, thereby preventing abuse was investigated. These enzymes will not be active when opioids are administered correctly. These possibilities are thoroughly investigated by the present project.

In the present example, the development of an appropriate enzyme system to eliminate opioids from solution can be shown. A peroxidase is used to produce an hydroxyl group in oxycodone while the such "activated" molecule is further transformed by the laccase. Moreover, optimized reaction conditions for effective conversion of the opioid solution preventing administration through injection are provided. Finally, the function of the system is verified by showing the inactivation of the opioid destroying enzymes proteolytically when the drugs are administered as foreseen.

Materials

The opioid that is investigated is oxycodone.

To achieve the elimination of oxycodone, the following enzymes are used: the horseradish peroxidase and a laccase originating from *Myceliophthora thermophila* (MtL). Glucose Oxidase (GOD, from *Aspergillus niger*) is used to generate $H_2O_2$ which is required for the peroxidase reaction.

Oxygen Measurements

To determine whether the laccase act on activated oxycodone an optical oxygen sensor is used. Laccases use oxygen as electron acceptor, consequently the oxygen concentration decreases upon substrate oxidation.

The conditions for the following reactions are shown in Table 1:

| | |
|---|---|
| Enzyme HRP | 10 U/ml |
| Enzyme Glucose Oxidase | 20 U/ml |
| Enzyme Laccase | 25 U/ml |
| Oxycodone | 10 mg/ml |
| Glucose | 10 mg/ml |
| Solvent | Distilled water |
| Temperature | Room temperature |

Measurements of Enzymatic Conversion Using HPLC

The kinetic of the enzymatic conversion of morphine was analyzed via HPLC-MS analysis.

Samples are taken at different time points (0, 2, 5, 10, 15, 30 minutes) during the reaction. 500 μL samples are taken and put into 500 μL of methanol (MeOH) to precipitate the enzyme. The solution is centrifuged using Vivaspin 500 and transferred to an HPLC vial. Then the solution is measured with following HPLC conditions shown in Table 2:

TABLE 2

Conditions for the HPLC-MS measurement of enzymatically oxidized oxycodone reaction rate determination

| | |
|---|---|
| Column | Agilent Technologies ZORBAX HILIC plus |
| Flow | 0.4 ml/min |
| Gradient | from 100% buffer 65 mM ammonia formiate pH 3 in MQ (18.2M) to 100% ACN within 15 min; total run 20 min |
| Injection volume | 1 μL |
| Column temperature | 40° C. |
| Detection | via MS-TOF in pos. mode |

The result can be evaluated by HPLC-MS measurement. From these data it will be clearly visible that oxycodone is converted enzymatically to a partly precipitated product. Further analysis of the exact reaction mechanism and reaction product is performed with the following methods: GPC and NMR.

Hydrogel

According to a preferred embodiment, the compositions according to the present inventions are provided as hydrogels. This involves the inclusion of another abuse deterrent approach, namely to create a system which changes the rheological properties of the reaction solution, i.e. the formation of a hydrogel. Hydrogels are very viscous and as a consequence, the drawing up with a needle is not possible.

Discussion

This study demonstrates an entirely new enzymatic approach for the development of abuse deterrent opioids. Oxycodone is successfully converted by the enzymes HRP and laccase (with cofactor generation by glucose oxidase), which is confirmed by oxygen consumption measurements and HPLC-MS analysis.

The reaction rate of the enzymes on oxycodone is analyzed via HPLC-MS measurement. Oxycodone is converted to a product which precipitated.

Overall the desired abuse prevention system based on enzyme polymerization is successfully developed. From the present results it is plausible that the present system is extendable in principle to all drugs, especially all opioids that have a laccase-reactive functional group.

2. Enzyme assays for selected and preferred oxycodone-processing enzymes are well known and available for most of the preferred enzymes listed herein. As an example, a known assay set-up for 2-oxoglutarate-dependent O-Demethylation is described hereinafter for illustrative reasons:

O-Demethylation (2-oxoglutarate-dependent)

The direct enzyme assay for 2-oxoglutarate-dependent dioxygenase activity can be performed using a reaction mixture of 100 mM Tris-HCl (pH 7.4), 10% (v/v) glycerol, 14 mM 2-mercaptoethanol, 1 mM alkaloid, 10 mM 2-oxoglutarate, 10 mM sodium ascorbate, 0.5 mM $FeSO_4$, and up to 100 μg of purified recombinant enzyme. Assays are carried out at 30° C. for 1 or 4 hours, stopped by immersing the reaction tube in boiling water for 5 min, and subjected to LC-MS/MS analysis. 2-Oxoglutaratedependent dioxygenase activity is also assayed using an indirect method based on the O-demethylation-coupled decarboxylation of [1-$^{14}$C]2-oxoglutarate. Briefly, the standard assay contained 10 μM of a 10% mole/mole (n/n) solution of [1-$^{14}$C]2-oxoglutarate (specific activity 55 mCi/mmol) diluted with 90% n/n unlabeled 2-oxoglutarate, 10 μM unlabelled alkaloid substrate, 10 mM sodium ascorbate, 0.5 mM iron sulfate, and 5 μg purified enzyme in a 500 μl buffered (100 mM Tris-HCl, 10% [v/v] glycerol, 14 mM 2-mercaptoethanol, pH 7.4) reaction. Assays are initiated by the addition of enzyme, incubated for 45 min at 30° C., and stopped by removing the $^{14}CO_2$-trapping glass fiber filters (Whatman grade GF/D, pretreated with NCS-II tissue solubilizer, Amersham Biosciences) from the reaction vial. For enzyme kinetic analyses, 10 μM of a 1% (n/n) solution of [1-$^{14}$C] 2-oxoglutarate (specific activity 55 mCi/mmol) diluted with 99% (n/n) unlabeled 2-oxoglutarate is used. Results from assays lacking an alkaloid substrate are subtracted from corresponding assays containing alkaloid substrates to account for the uncoupled consumption of 2-oxoglutarate. Kinetic data for e.g. T6ODM can be obtained by varying the substrate concentrations in the reaction between 1 and 500 μM at a constant 2-oxoglutarate concentration of 500 μM. Conversely, the 2-oxoglutarate concentration can be varied between 1 and 500 μM at a constant substrate concentration of 30 μM, which produces the maximum reaction velocity.

Kinetic data for e.g. CODM can be obtained by varying the 500 μM, and varying the 2-oxoglutarate concentration between 1 and 500 μM at a constant codeine concentration of 50 μM. Saturation curves and kinetic constants can be calculated based on Michaelis-Menten kinetics using FigP v. 2.98 (BioSoft, Cambridge, UK; http://www.biosoft.com). The release of formaldehyde upon alkaloid O-demethylation can be monitored using a fluorescence-based modification of the Nash assay. Nash reagent is prepared by adding 0.3 ml of glacial acetic acid and 0.2 ml acetyl acetone to 100 ml of 2 M ammonium acetate. Enzyme assays can be performed as described above, except that unlabelled 2-oxoglutarate is used and the reactions are quenched by the addition of 2 volumes of Nash reagent, followed by a 10 min incubation period at 60° C. to convert formaldehyde to diacetyldihydrolutidine (DDL). The fluorescence of DDL can be recorded using a Cary Eclipse fluorescence spectrophotometer (Varian; www.varianinc.com) at $\lambda_{ex}$=412 nm and $\lambda_{em}$=505 nm. The acylcyclohexanediones, prohexadione calcium or trinexapac-ethyl, can be tested as possible enzyme inhibitors at concentrations up to 500 μM using 100 μM 2-oxoglutarate in a standard assay.

3. Laccase Mediator System (LMS): Elimination of Opioids

Mediators can be used as electron shuttles to facilitate the oxidation of complex substrates that could otherwise not be oxidized by a laccase on its own. While opioids containing a phenolic group readily serve as substrate for laccases, other opioids such as oxycodone, methadone or dihydrocodeine are not as readily oxidized. The substrate range of laccases can be increased with mediators: These often small molecules are oxidized by the laccase in a first step and then react in their oxidized state with a broad variety of target substrates.

Figure 3:
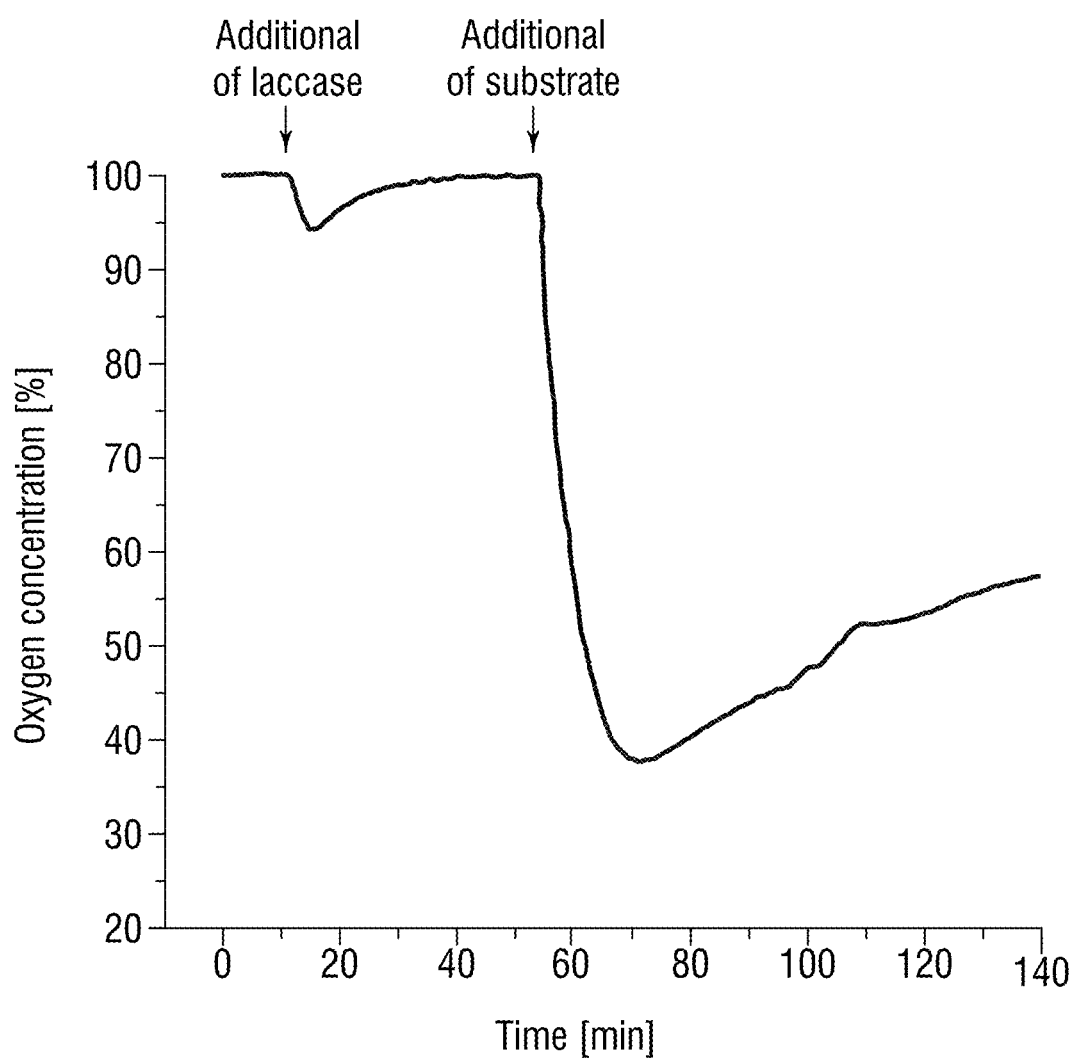
FIG. 3 shows oxygen concentration measurement for the laccase mediator system.

During the reaction oxygen acts as electron acceptor and is reduced to water by laccases while the mediators are oxidized. The concentration of oxygen was measured as described above. Oxygen is consumed until the mediator is fully oxidized. An open experimental setup was chosen; hence the oxygen concentration can recover to its starting value. The second step of the reaction is initiated by addition of the target substrate, which is consequently oxidized by the mediators. The now reduced mediators can again be targeted by the laccases, which leads to a decline in oxygen concentration once more (see FIG. 3).

In the present experiments the final reaction mixtures contained 0.2 to 6 mM mediator, 1-10 units of laccase per ml and 100-3000 mg L$^{-1}$ opioid.

2.1. LMS and Oxycodone

Figure 4:
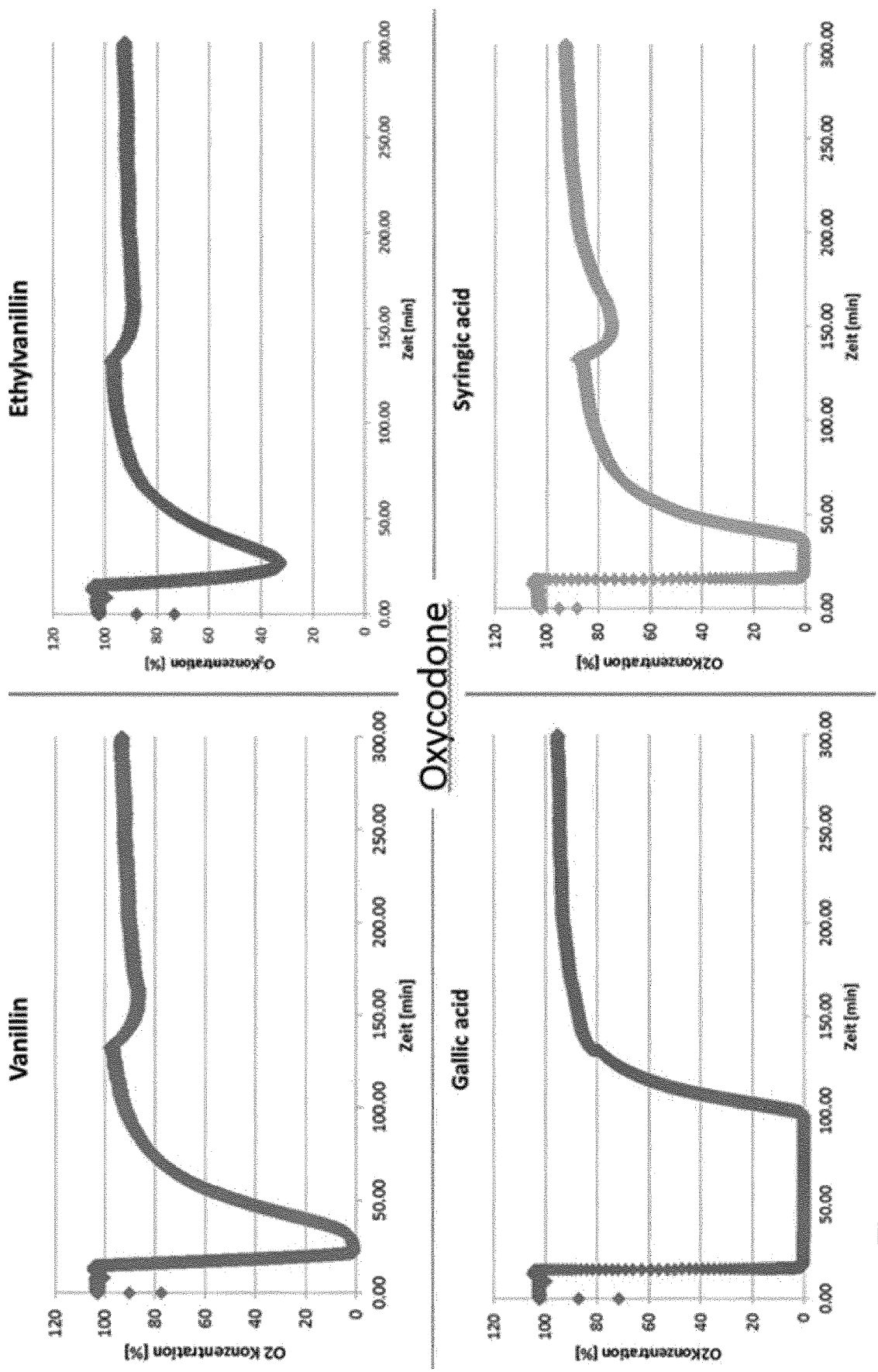
FIG. 4 shows oxygen concentration measurement for the laccase mediator system and oxycodone, with the mediators vanillin, ethylvanillin, gallic acid and syringic acid.

FIG. 4 shows the oxygen concentration levels for oxycodone in the laccase mediator system. The different mediators were used at concentrations of 2 mM with 10 units laccase ml$^{-1}$ and 1000 mgL$^{-1}$ oxycodone. The first drop in oxygen concentration represents the oxidation of the respective mediators with the laccase, the second drop—which took place just after the addition of the opioid—was due to the subsequent oxidation of the opioid.

The mediators vanillin, ethylvanillin and syringic acid showed a drop in oxygen concentration after the addition of oxycodone, which can be seen in FIG. 4. This shows an oxidation of oxycodone.

To further confirm the oxidation and elimination of oxycodone HPLC-MS/TOF measurements were done.

The concentrations were determined with a liquid chromatography-electrospray ionization-time of flight (HPLC-ESI-TOF) mass spectrometer from Agilent (A1260 series, Agilent US). The substances contained in the samples were separated by a Zorbax Hilic Plus, 2.1×100 mm, 3.5 μm (Agilent, US) column. The gradient was set to 100% mobile phase A (65 mM ammonium formiate pH 3.2) with a flow rate of 0.4 mL min$^{-1}$ at 40° C. and changed to 100% mobile phase B (acetonitrile) in 15 minutes with an injection volume of 1 μL. The spectra were acquired over the m/z range from 100 to 3000 at a scan rate of two spectra per second. The standard curve for each opioid was performed with corresponding standards ranging from 0.001 to 50 mg L.

Figure 5:
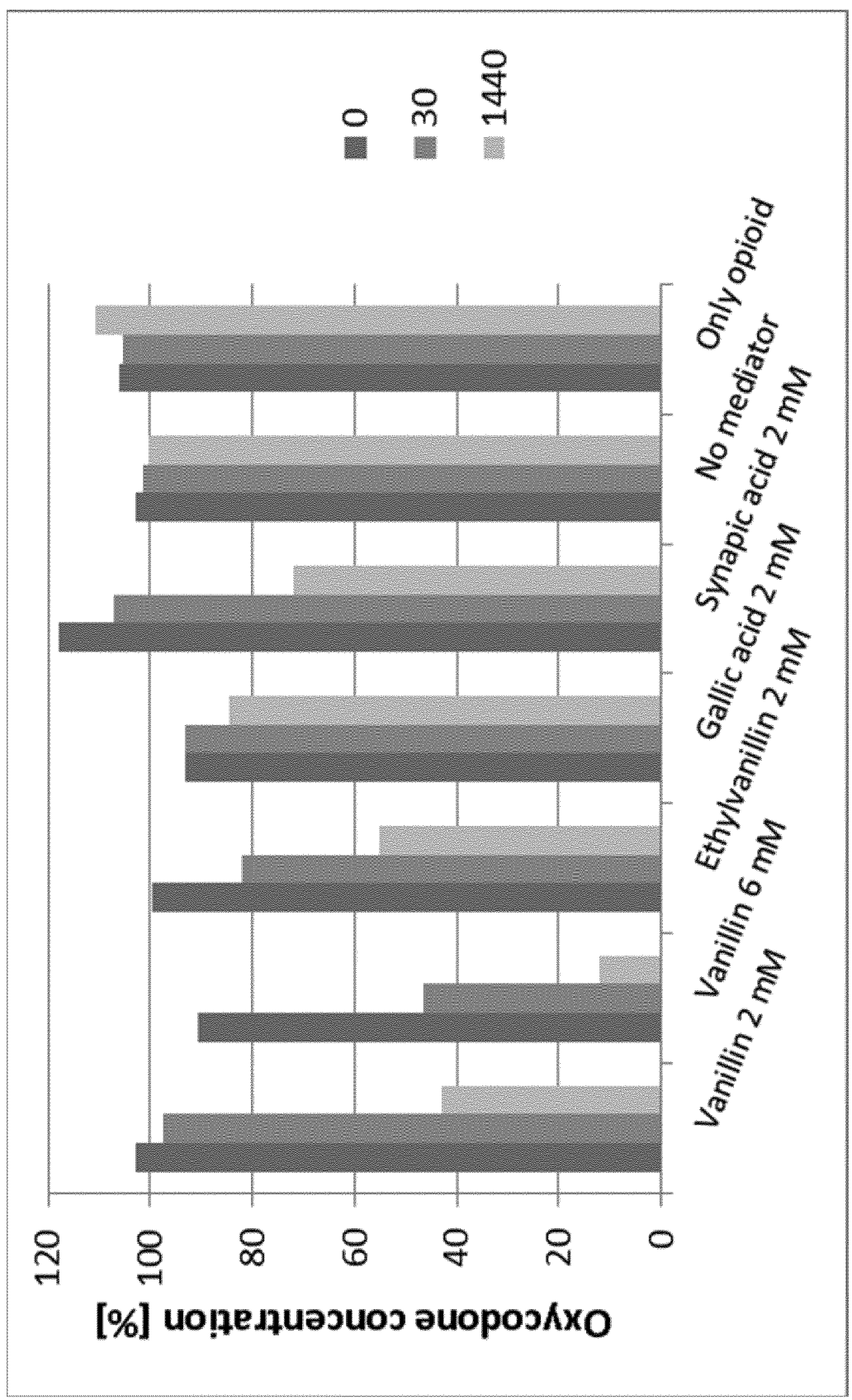
FIG. 5 shows oxycodone concentrations in percent for various LMS experiments with oxycodone and the respective controls.
Figure 6:
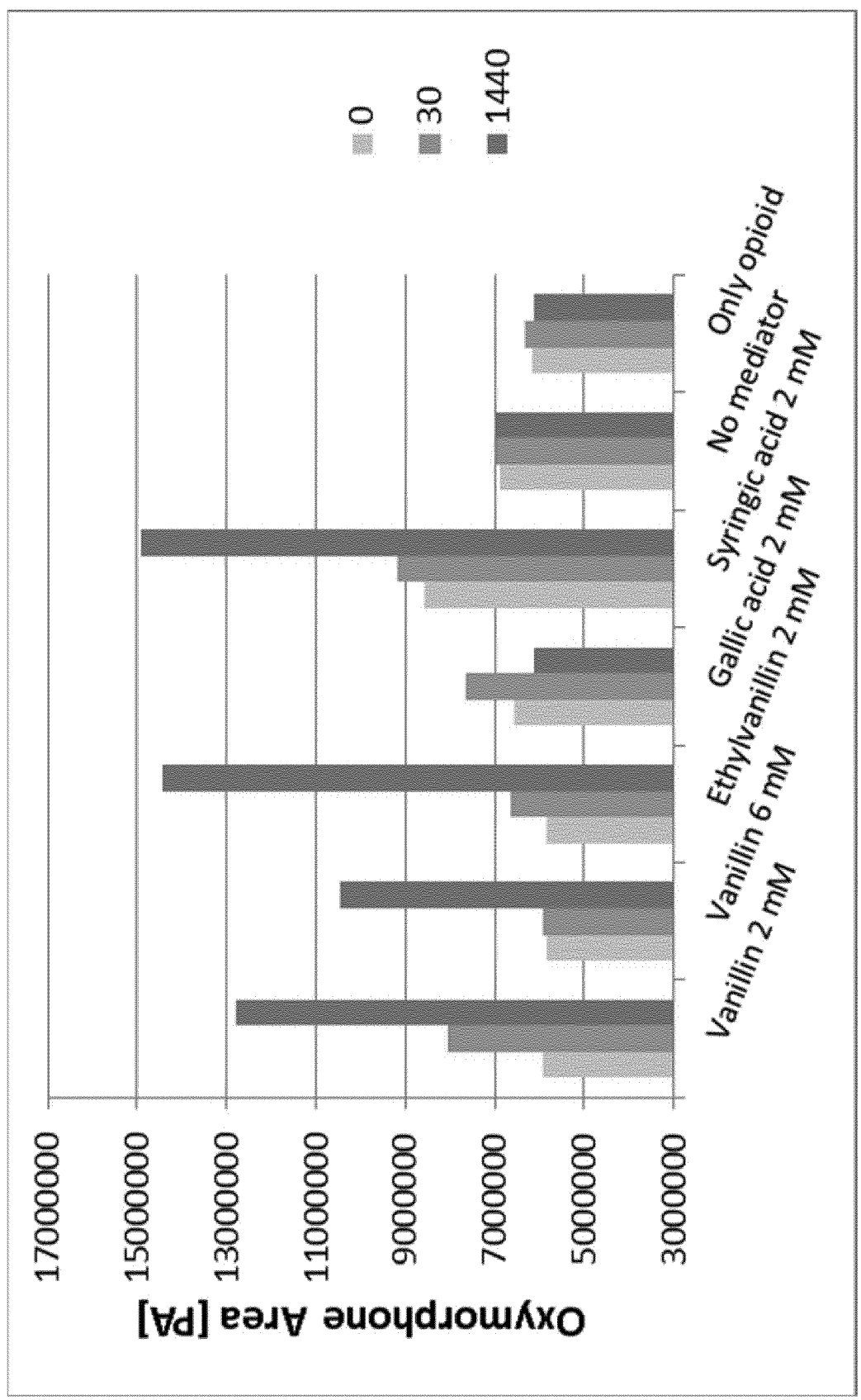
FIG. 6 shows peak area [PA] found by MS-TOF analysis for the molecule formula $C_{17}H_{19}NO_4$, which is oxymorphone.

In addition to the reactions shown in FIG. 4, the mediator vanillin was used at a higher concentration (6 mM). The results can be seen in FIG. 5 and FIG. 6. The decrease in oxycodone concentration was confirmed. One of oxycodone's main degradation products, oxymorphone, was found in all samples. Oxymorphone is an impurity of oxycodone and is therefore present even in the controls where no laccase or mediator were used. However, an increase in peak area of oxymorphone over time can only be observed for oxycodone in combination with the laccase mediator system. The only mediator that had no apparent effect on oxycodone was gallic acid, an observation that was supported by both the oxygen concentration measurement and the MS-TOF analysis.

4. Inactivation of Enzymes—SGF and Proteases

Figure 7:
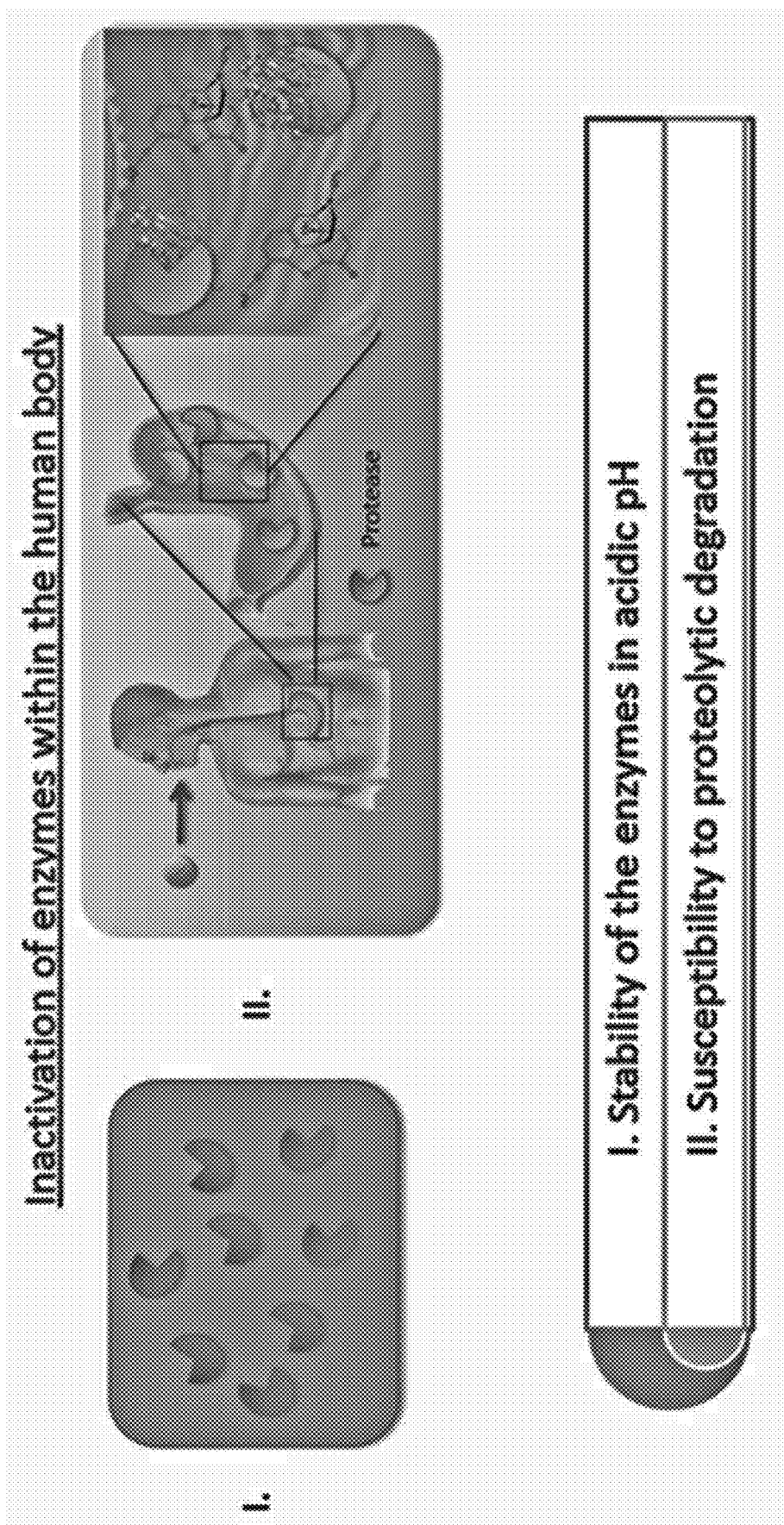
FIG. 7 shows inactivation of enzymes within the human body.

The inactivation of the enzymes when the drugs are administered as foreseen is an integral part of the invention. Inactivation can be achieved both by acidic denaturation and proteolytic degradation (FIG. 7).

To assess the feasibility of the inactivation methods, protease digestion assays as well as enzyme stability trials in various pH levels were done.

4.1. Pepsin Digestion Assay

The method used to demonstrate pepsin digestion of MTL was described by Thomas et al. (Thomas et al., Regul. Toxicol. Pharmacol. 39 (2004), 87-98) and is a standardized protocol using simulated gastric fluid (SGF). SGF contains 0.084 M HCl, 0.035 M NaCl, 4000 U of pepsin per reaction mixture and has a pH level of 1.2 according to the United States Pharmacopeia (1995). A ratio of 10000 Units of pepsin activity to 1 mg of test protein was used throughout the assay, which is based on an evaluation of the average activity of pepsin recommended in the United States Pharmacopeia (24$^{th}$ edition, 2000) with some modifications. Pepsin (ref. # P7000) was purchased from Sigma-Aldrich (US). All proteins that were used were dissolved in 50 mM Tris-HCl (pH 9.5) at a concentration of 5 mg mL$^{-1}$. The reaction mixture contained 1.52 mL of SGF preheated to 37° C. before the addition of 0.08 mL of protein solution (Thomas et al., 2004). The mixture was placed into a thermomixer at 37° C. and was shaken at 400 rpm. For denaturating SDS-polyacrylamide gel electrophoresis (SDS-PAGE) analysis samples of 160 μl were removed at 0 minutes, 0.5 minutes, and 15 minutes after initiation.

4.2 SDS-PAGE Analysis

SDS-PAGE was performed to analyze and visually inspect stained protein bands whether the protein band is still intact or fragmented after the digestion assay. Precast tris-glycin gels (ref. #456-1086) with 4-15% polyacrylamide, 10× tris-glycine-SDS (TGS) buffer (ref. #1610772) and 4× Laemmli sample buffer (ref. #1610747), were purchased from Bio-Rad Laboratories (Hercules, USA). The 4× Laemmli buffer was diluted 10:1 with 2-mercaptoethanol before usage. The following sample preparation method was described by Thomas et al (Thomas et al. 2004).

Each 160 μl of the digestion samples was quenched by adding μl of 200 mM NaHCO$_3$ as neutralization step and 56 μl 4× Laemmli (Laemmli 1970) buffer for electrophoresis.

Samples were immediately heated up to 99° C. for 10 minutes and analyzed directly or stored at −20° C. Control samples for pepsin and test protein stability (SGF without pepsin but with test protein) were treated in the same way as described above. The zero time point digestion samples were prepared differently, since pepsin immediately starts to digest and auto-digest as soon as it is in solution. Before adding the test protein, pepsin was already denatured in quenching solution and heated up to 99° C. for 5 minutes. Afterwards the sample was heated again for 5 minutes to ensure proper denaturation of the test protein. 15 μl of each sample and 5 μl of prestained protein marker IV (ref. #27-2110, Peqlab) were loaded onto the gel and were subsequently run in tris-glycin running buffer for 30-45 minutes at 200 V. For visualization the gels were incubated with Coomassie-blue staining solution (0.1% w v$^{-1}$ Coomassie R250, 10% v v$^{-1}$ acetic acid, 45% v v$^{-1}$ methanol) for 30 minutes followed by a destaining step (10% v v$^{-1}$ acetic acid, 40% v v$^{-1}$ methanol) for 10-30 minutes.

Figure 8:
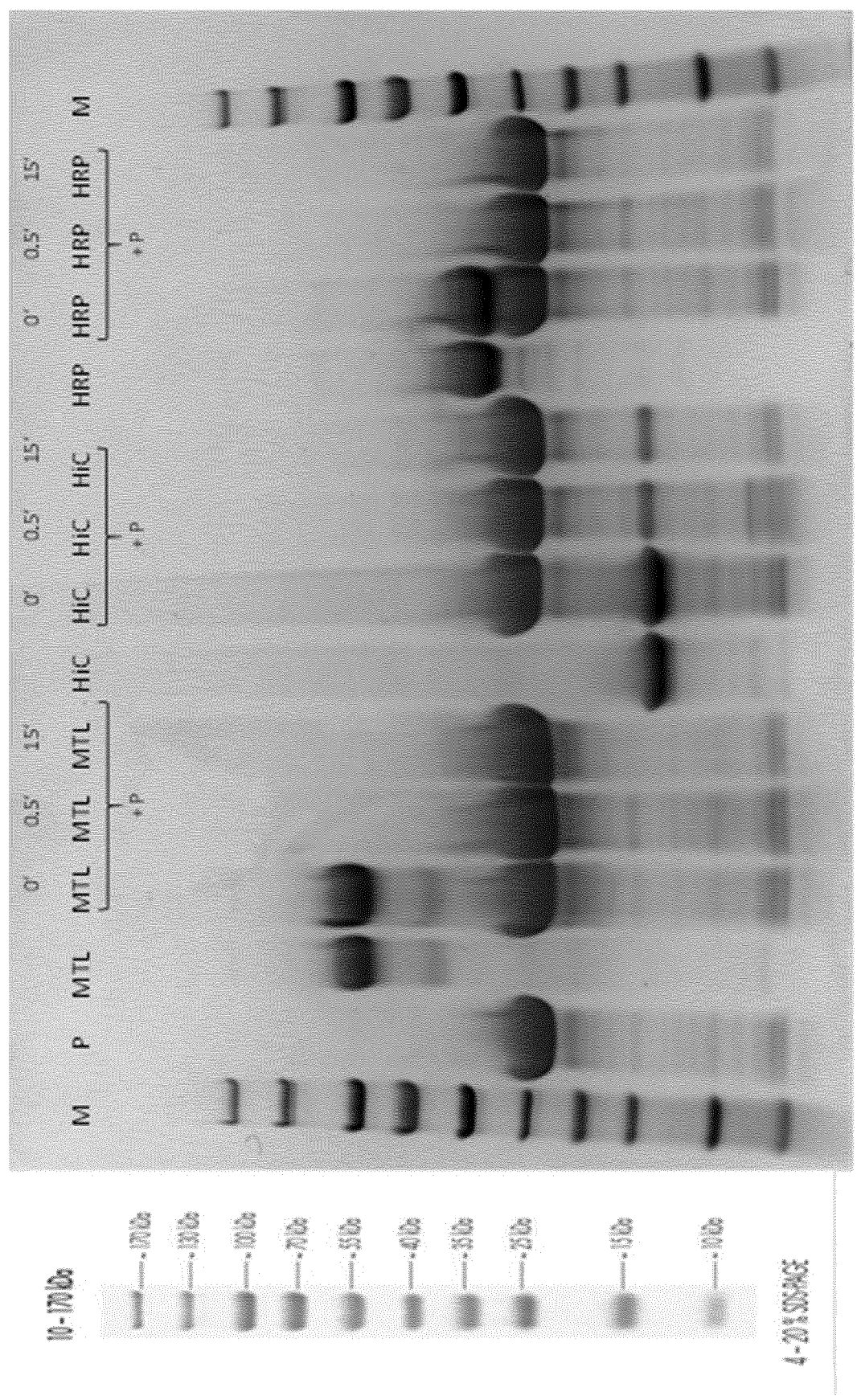
FIG. 8 shows SDS-Page gel showing the proteolytic degradation of different enzymes, namely *Myceliophthora thermophila* laccase MTL, *Humicola insolens* cutinase HiC and horse radish peroxidase HRP.

The results of the proteolytic enzyme degradation can be seen in FIG. 8. MTL and HRP are very susceptible to proteolytic degradation, as their respective protein bands vanished within seconds. The HiC displayed a moderate decrease in concentration.

4.3 Laccase Stability Assay

To establish a pH profile for MTL enzyme activities were measured at different pH levels from acidic to neutral (pH 2.5-pH 7) over time using ABTS as substrate. For every pH level MTL was diluted 1:100 in the respective buffer and was incubated for one hour and room temperature. Enzyme activity was measured at distinctive time points. Activity was measured and calculated by ABTS-assay (described above), using different extinctions coefficients for each pH level (pH7: ε=11.38 mL μmol$^{-1}$ cm$^{-1}$, pH6: ε=23.34 mL μmol$^{-1}$ cm$^{-1}$, pH5: ε=32.03 mL μmol$^{-1}$ cm$^{-1}$, pH4: ε=35.49 mL μmol$^{-1}$ cm$^{-1}$, pH3, 2: ε=36.00 mL μmol$^{-1}$ cm$^{-1}$; master thesis ("Laccases as effective siccatives in alkyd resins"), Scholz, 2015.

Figure 9:
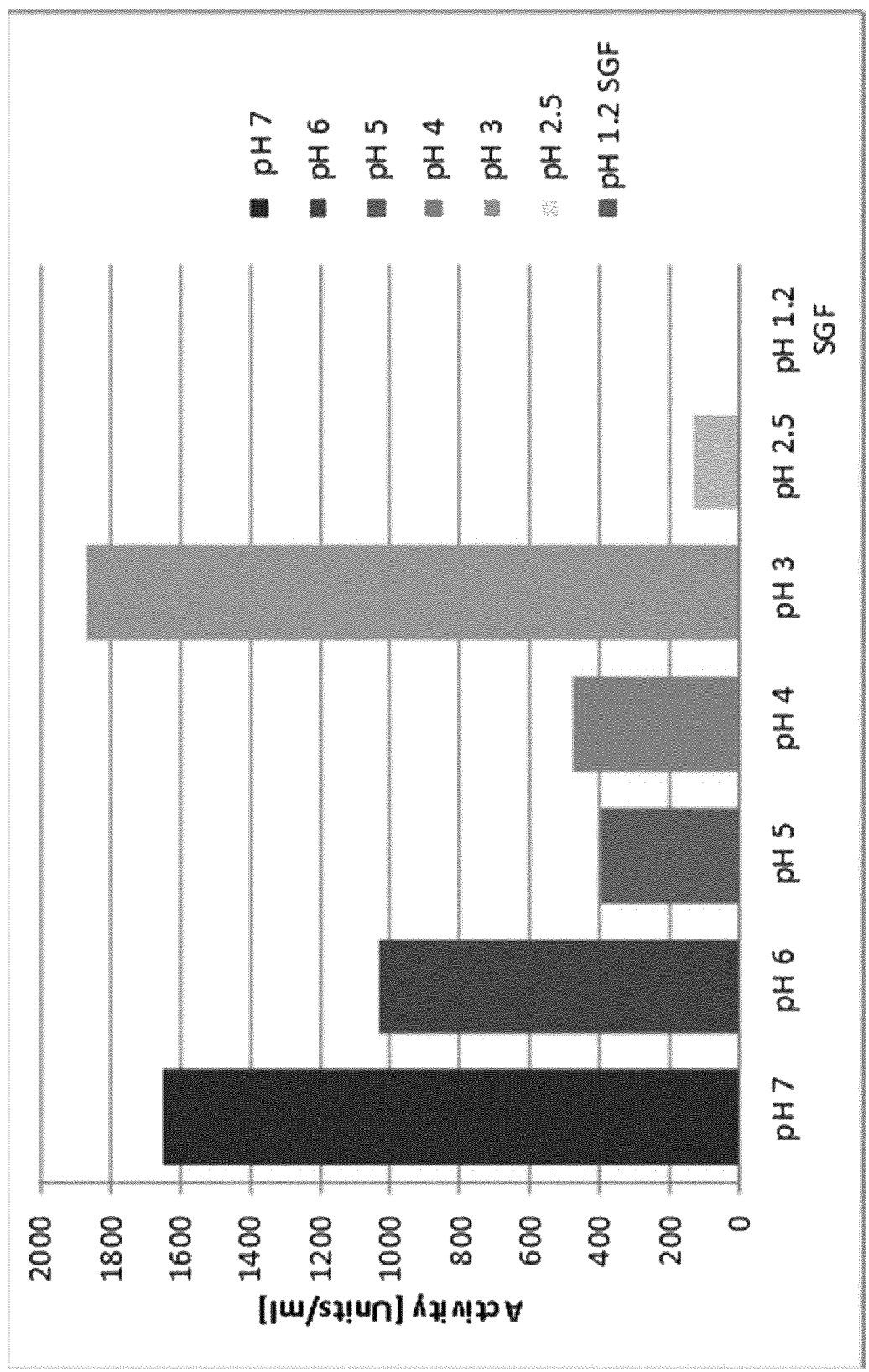
FIG. 9 shows pH activity profile of MTL using ABTS as substrate.
Figure 10:
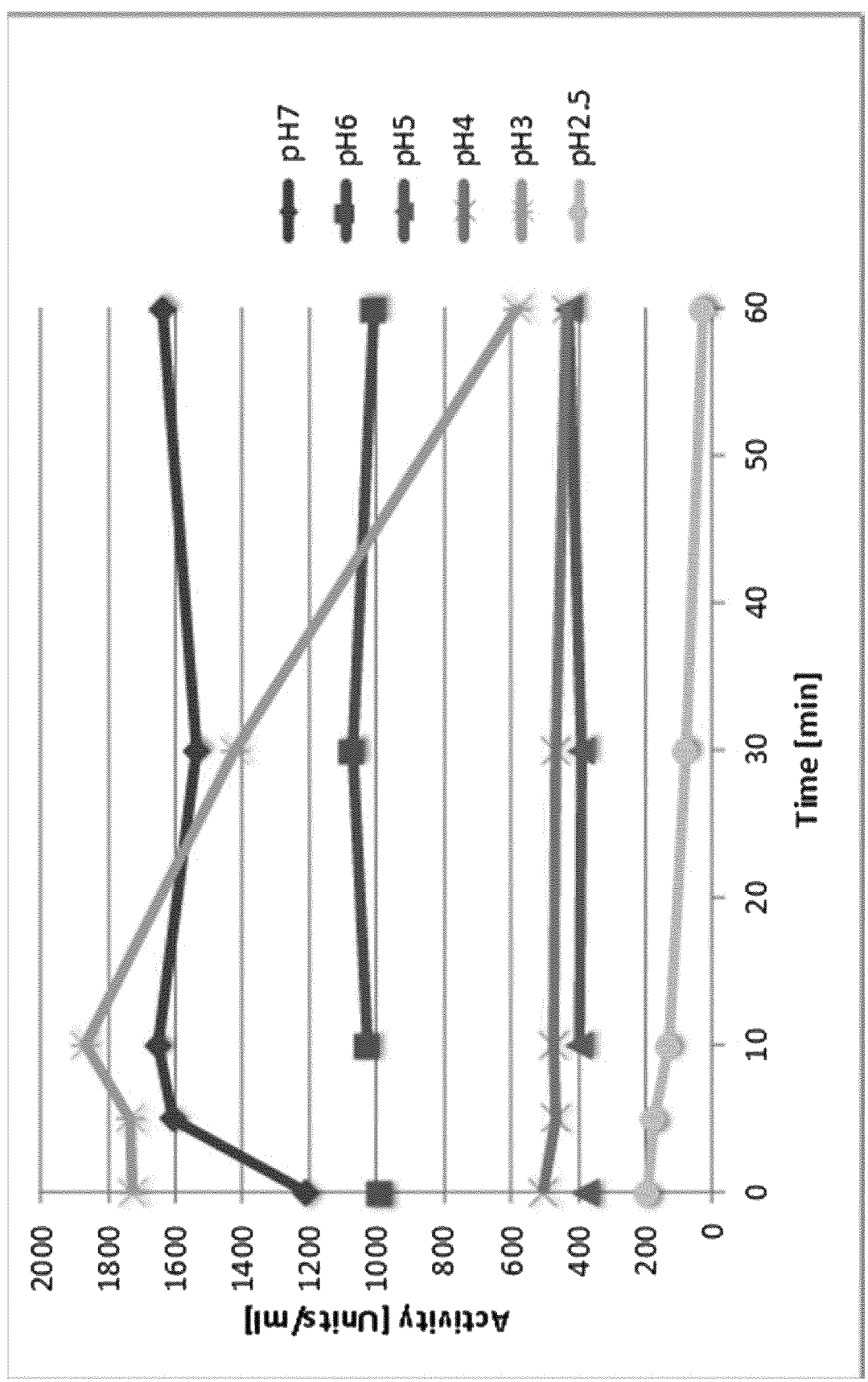
FIG. 10 shows the stability profile of MTL in different pH levels over time.

The pH profile of the MTL can be seen in FIG. 9, whereas the stability profile in different pH levels over time is shown in FIG. 10. MTL has two activity maxima, one at pH 7 and the second at pH 3 and shows no activity at SGF medium conditions. The stability profile indicates that MTL remains most of its activity at a pH range from 4 to 7 but loses activity rather quickly at lower pHs.

PREFERRED EMBODIMENTS

The present invention therefore relates to the following preferred embodiments:

1. Pharmaceutical composition comprising oxycodone or a pharmaceutically acceptable salt thereof and an oxycodone-processing enzyme, wherein oxycodone is contained in the pharmaceutical composition in a storage stable, enzyme-reactive state and under conditions wherein no enzymatic activity acts on oxycodone.

2. Pharmaceutical composition according to embodiment 1, wherein the enzyme is selected from the group of oxidoreductases and/or transferases and/or hydrolases, especially a monooxygenase, a peroxidase, a peroxygenase and/or a sulfotransferase.

3. Pharmaceutical composition according to embodiment 1 or 2, wherein the enzyme catalyses O-demethylation, N-demethylation, keto-reduction, N-oxidation, epoxy-hydroxylation of oxycodone or addition of molecules, especially glucuronidation, sulfation and acetylation, to oxycodone.

4. Pharmaceutical composition according to any one of embodiments 1 to 3, wherein oxycodone is a salt, hydrate, solvate or prodrug of oxycodone, preferably a salt selected from the group of hydrochloride, bitartrate, tartrate, camphorsulphonate, phenylpriopionate, sulphate, pectinate, phosphate, methyiodide, hydroiodide and terephthalate or a prodrug form.

5. Pharmaceutical composition according to any one of embodiments 1 to 4, wherein the pharmaceutical composition is selected from a tablet, a mini-tablet, a coat-core tablet (coated tablet), a bi-layer tablet, a multi-layer tablet, a capsule, a pellet, a MUPS (multiple unit pellet system), a granulate, a powder, especially coated, sugar-coated and/or functionally coated (e.g. enteric coated) forms thereof.

6. Pharmaceutical composition according to any one of embodiments 1 to 5, wherein the composition comprises a coated oxycodone-processing enzyme.

7. Pharmaceutical composition according to any one of embodiments 1 to 6, wherein oxycodone is contained in an amount of 0.1 to 5 000 mg, preferably 0.5 to 1 000 mg, especially 1 to 500 mg, per dosage unit.

8. Pharmaceutical composition according to any one of embodiments 1 to 7, wherein the composition comprises co-factors of the oxycodone-processing enzyme, preferably H and/or electron donors and acceptors, especially NAD(P) H, FMN, FAD, ferredoxin, 2-oxoglutarate, and/or hemes; or donors for the groups to be added to oxycodone, especially acetyl-Coenzyme A (ac-CoA) or UDP-glucuronate.

9. Pharmaceutical composition according to any one of embodiments 1 to 8, wherein the composition comprises a further abuse-deterrent feature, preferably selected from the group a physical or chemical barrier, especially increased tablet hardness, a drug antagonist, an aversion component, an abuse-deterrent delivery system and a prodrug, especially a physical barrier or an aversion component, especially a gelling agent and/or a non-gelling viscosity-increasing agent.

10. Pharmaceutical composition according to any one of embodiments 1 to 9, wherein the composition comprises a matrix containing 1 to 80 wt. % of one or more hydrophobic or hydrophilic polymers, preferably a matrix comprising agar, alamic acid, alginic acid, carmellose, carboxymethylcellulose sodium, carbomer, carrageenan, chitosan, especially carboxymethylchitosan, catechol, copovidone, dextrin, gelatin, hydroxyethyl cellulose, hydroxypropyl cellulose, hydroxypropyl methylcellulose, methacrylic acid copolymers, methylcellulose derivatives, microcrystalline cellulose, polyacrylic acid, polyalkylene oxide, especially polyethylene glycol, polyvinyl alcohol, polyvinyl acetate, povidone, propylene glycol alginate, a polyvinylcaprolactam-polyvinyl acetate-polyethylene glycol graft co-polymer, pullulan, silicon dioxide, sodium alginate, starch, vinylpyrrolidone-vinyl acetate copolymers; or of a non-polymer matrix former, preferably microcrystalline wax, fatty alcohols and fatty acids, especially stearyl alcohol, cetyl stearyl alcohol, stearic acid, palmitic acid or salts and mixtures thereof, mono-, di- and triglycerides of saturated fatty acids with a chain length between 16 and 22 carbon atoms and a mixture of such mono- di- and triglycerides.

11. Pharmaceutical composition according to any one of embodiments 1 to 10, wherein the composition is storage stable, preferably by comprising less than 5%, especially less than 1%, enzyme-processed oxycodone after 6 month storage at 25° C. under dry conditions.

12. Pharmaceutical composition according to any one of embodiments 1 to 11, further comprising a hydrogel-forming component and/or a crosslinker, preferably chitosan and/or catechol or carboxymethylchitosan and/or vanillin.

13. Pharmaceutical composition according to any one of embodiments 1 to 12, wherein the composition is a modified release composition, especially a prolonged release composition.

14. Pharmaceutical composition according to any one of the preceding embodiments, wherein the composition renders immediate release, modified release, or a combination thereof.

15. Pharmaceutical composition according to any one of embodiments 1 to 14, wherein the enzyme is selected from the group of 3-alpha-hydroxysteroid 3-dehydrogenase (EC 1.1.1.213), cytochrome P450 (EC 1.14), especially non-heme iron-dependent monooxygenase (EC 1.14.16), copper-dependent monooxygenases (EC 1.14.17 and EC 1.14.18), the CYP2C subfamily; CYP2D6; unspecific monooxygenase (EC 1.14.14.1), Codeine 3-O-demethylase (CODM; EC 1.14.11.32), CYP1-3 (EC 1.14.14.1), preferably CYP3A, CYP1A, CYP2B, CYP2C and CYP2D, especially CYP3A4, CYP3A5, CYP3A7, CYP1A2, CYP2B6, CYP2C9, CYP2C19, and CYP2D6; peroxidases (EC 1.11.1 and EC 1.11.2), preferably horseradish peroxidase (EC 1.11.1.7) and fungal unspecific peroxygenase (EC 1.11.2.1); carbonyl reductase (NADPH) (EC 1.1.1.184), preferably dihydromorphinine ketone reductase (DMKR; types I to V), dihydrocodeinone ketone reductase (DCKR, types I and II) or morphine 6-dehydrogenase (EC 1.1.1.218); flavin-dependent monooxygenases (EC 1.13.12 and EC 1.14.13), especially flavin-containing monooxygenase (EC 1.14.13.8); microsomal epoxide hydrolase (EC 3.3.2.9), cofactor-independent monooxygenase; epoxide hydratase (EC 3.3.2.3 and 4.2.1.63), and soluble epoxide hydrolase (EC 3.3.2.10); UDP-glucuronosyltransferase (EC 2.4.1.17), preferably UGT1 and UGT2 enzymes, especially UGT1.1 and UGT2B7; bilirubin-glucuronoside glucuronosyltransferase (EC 2.4.1.95); ac(et)yltransferase (EC 2.3), sulfotransferases (EC 2.8.2), CoA-transferase (EC 2.8.3), especially N-acetyltransferase (NAT, EC 2.3.1) and O-acetyltransferase (OAT; EC 2.3.1).

16. Pharmaceutical composition according to any one of embodiments 1 to 15, comprising a further enzyme, preferably a further oxycodone-processing enzyme or an enzyme further processing the processed oxycodone forms, especially laccase (EC 1.10.3.2).

17. Pharmaceutical composition according to any one of embodiments 1 to 16, wherein the composition comprises oxycodone alone or in combination with a non-opioid analgesic, preferably with ibuprofen, diclofenac, naproxen, par-acetamol and acetyl-salicylic acid.

18. Pharmaceutical composition according to any one of embodiments 1 to 17, wherein the enzyme essentially does not act on the drug in vivo when the composition is administered in the intended way and intact.

19. Pharmaceutical composition according to any one of embodiments 1 to 18, wherein the enzyme is present in the composition in an essentially non-releasable form when the composition is administered in the intended way and intact.

20. Pharmaceutical composition according to any one of embodiments 1 to 19, wherein the enzyme is deactivated in vivo.

21. Pharmaceutical compositions according to any one of embodiments 1 to 20, with a moisture content below 10%, preferably with a moisture content of below 5%, especially with a moisture content of below 2%.

22. Method for manufacturing a pharmaceutical composition according to any one of embodiments 1 to 21 comprising the steps of mixing oxycodone or a pharmaceutically acceptable salt, hydrate, solvate, ester or prodrug thereof with the oxycodone-processing enzyme and finishing the mixture to a pharmaceutical composition.

23. Method for manufacturing a pharmaceutical composition according to any one of embodiments 1 to 21 comprising the steps of providing oxycodone or a pharmaceutically acceptable salt, hydrate, solvate, ester or prodrug thereof and the oxycodone-processing enzyme in separated form and finishing the separated oxycodone or a pharmaceutically acceptable salt, hydrate, solvate, ester or prodrug thereof and oxycodone-processing enzyme to a pharmaceutical composition.

24. Pharmaceutical composition according to any one of embodiments 1 to 21 for use in the treatment of drug addiction.

25. Pharmaceutical composition according to any one of embodiments 1 to 21 for use in the treatment of pain.

26. Method of administration the pharmaceutical composition according to any one of embodiments 1 to 21 to a patient in need thereof, wherein the pharmaceutical composition is orally administered to this patient in an effective amount and wherein the oxycodone-processing enzyme is automatically deactivated in the course of this oral administration.

The invention claimed is:

1. A pharmaceutical composition comprising oxycodone or a pharmaceutically acceptable salt thereof and an oxycodone-processing enzyme, wherein oxycodone is contained in the pharmaceutical composition in a storage stable, enzyme-reactive state and under conditions wherein no enzymatic activity acts on oxycodone,
wherein the oxycodone-processing enzyme is selected from 3-alpha-hydroxysteroid 3-dehydrogenase, cytochrome P450, copper-dependent monooxygenases, the CYP2C subfamily; CYP2D6; unspecific monooxygenase, Codeine 3-0-demethylase, CYP1-3, horseradish peroxidase, carbonyl reductase, flavin-dependent monooxygenases, microsomal epoxide hydrolase, cofactor independent monooxygenase, epoxide hydratase, soluble epoxide hydrolase, UDP-glucuronosyltransferase, bilirubin-glucuronoside glucuronosyltransferase, ac(et)yltransferase, sulfotransferases, and CoA-transferase.

2. The pharmaceutical composition according to claim 1, wherein oxycodone is a salt, hydrate, solvate or prodrug of oxycodone.

3. The pharmaceutical composition according to claim 1, wherein the pharmaceutical composition is selected from the group consisting of a tablet, a mini-tablet, a coated tablet, a bi-layer tablet, a multi-layer tablet, a capsule, a pellet, a multiple unit pellet system, a granulate, and a powder.

4. The pharmaceutical composition according to claim 1, wherein the composition further comprises a coated oxycodone-processing enzyme.

5. The pharmaceutical composition according to claim 1, wherein oxycodone is contained in an amount of 0.1 to 5.000 mg per dosage unit.

6. The pharmaceutical composition according to claim 1, wherein the composition further comprises a cofactor of the oxycodone-processing enzyme.

7. The pharmaceutical composition according to claim 1, wherein the composition is storage stable.

8. The pharmaceutical composition according to claim 1, further comprising an additional enzyme.

9. The pharmaceutical composition according to claim 1, wherein the composition comprises oxycodone alone or in combination with a non-opioid analgesic.

10. A method for treating pain and/or drug addiction, the method comprising administering the pharmaceutical composition of claim 1 to a subject in need thereof to treat pain and/or drug addiction.

11. A method for manufacturing a pharmaceutical composition according to claim 1, comprising mixing oxycodone or a pharmaceutically acceptable salt, hydrate, solvate, ester or prodrug thereof with the oxycodone-processing enzyme and finishing the mixture to a pharmaceutical composition.

12. A method for manufacturing a pharmaceutical composition according to claim 1 comprising providing oxycodone or a pharmaceutically acceptable salt, hydrate, solvate, ester or prodrug thereof and the oxycodone-processing enzyme in separated form and finishing the separated oxycodone or a pharmaceutically acceptable salt, hydrate, solvate, ester or prodrug thereof and oxycodone-processing enzyme to a pharmaceutical composition.

\* \* \* \* \*